United States Patent
Lee et al.

(10) Patent No.: US 10,327,926 B2
(45) Date of Patent: Jun. 25, 2019

(54) IMPLANTABLE AND LUMEN-SUPPORTING STENTS AND RELATED METHODS OF MANUFACTURE AND USE

(71) Applicant: CELONOVA BIOSCIENCES, INC., San Antonio, TX (US)

(72) Inventors: Michael J. Lee, Santa Rosa, CA (US); Stuart Earl Karl, Windsor, CA (US); Riley King, Rohnert Park, CA (US)

(73) Assignee: CELONOVA BIOSCIENCES, INC., San Antonio, TX (US)

( * ) Notice: Subject to any disclaimer, the term of this patent is extended or adjusted under 35 U.S.C. 154(b) by 119 days.

(21) Appl. No.: 15/234,742

(22) Filed: Aug. 11, 2016

(65) Prior Publication Data
US 2016/0346105 A1    Dec. 1, 2016

Related U.S. Application Data

(63) Continuation of application No. 13/226,476, filed on Sep. 6, 2011, now Pat. No. 9,445,927, which is a
(Continued)

(51) Int. Cl.
| | | |
|---|---|---|
| *A61F 2/06* | (2013.01) | |
| *A61F 2/915* | (2013.01) | |
| *A61F 2/91* | (2013.01) | |

(52) U.S. Cl.
CPC ............ *A61F 2/915* (2013.01); *A61F 2/91* (2013.01); *A61F 2002/91541* (2013.01);
(Continued)

(58) Field of Classification Search
CPC ... A61F 2/91; A61F 2/915; A61F 2002/91558
See application file for complete search history.

(56) References Cited

U.S. PATENT DOCUMENTS

| | | |
|---|---|---|
| 5,135,536 A | 8/1992 | Hillstead |
| 5,292,331 A | 3/1994 | Boneau |
(Continued)

FOREIGN PATENT DOCUMENTS

| | | | | |
|---|---|---|---|---|
| WO | WO 9301221 A1 * | 1/1993 | ............. | C07F 9/091 |
| WO | WO-93/15775 A1 | 8/1993 | | |
(Continued)

*Primary Examiner* — Andrew M Iwamaye
(74) *Attorney, Agent, or Firm* — Mannava & Kang, P.C.; Carol L. Bunner

(57) ABSTRACT

There is disclosed an implantable medical stent system, including: a radially expandable stent comprising a filamental structure in a pattern surrounding a bore to form a substantially tubular wall along a length relative to a longitudinal axis; in which the filamental structure includes at least one arcuate crown with a crown peak having a radius of curvature located along a reference axis, and first and second arcuate crown shoulders on first and second sides, respectively, of the reference axis; in which the filamental structure also includes at least one pair of first and second elongated struts extending from the first and second crown shoulders, respectively; the first and second elongated struts have a region of constant maximum width at an intermediate portion and tapering toward the first and second crown shoulders.

19 Claims, 19 Drawing Sheets

Related U.S. Application Data continuation of application No. 11/943,527, filed on Nov. 20, 2007, now abandoned.

(60) Provisional application No. 60/981,433, filed on Oct. 19, 2007.

(52) U.S. Cl.
CPC ............... *A61F 2002/91558* (2013.01); *A61F 2002/91575* (2013.01); *A61F 2210/0014* (2013.01); *A61F 2210/0076* (2013.01); *A61F 2230/0054* (2013.01); *A61F 2230/0069* (2013.01); *A61F 2250/0018* (2013.01); *A61F 2250/0029* (2013.01); *A61F 2250/0031* (2013.01); *A61F 2250/0032* (2013.01); *A61F 2250/0036* (2013.01); *A61F 2250/0068* (2013.01)

(56) References Cited

U.S. PATENT DOCUMENTS

| | | | |
|---|---|---|---|
| 6,042,606 A | | 3/2000 | Frantzen |
| 6,083,257 A | * | 7/2000 | Taylor ............... A61F 2/90 623/1.46 |
| 6,203,569 B1 | | 3/2001 | Wijay |
| 6,231,598 B1 | | 5/2001 | Berry et al. |
| 6,293,967 B1 | | 9/2001 | Shanley |
| 6,312,459 B1 | | 11/2001 | Huang et al. |
| 6,416,543 B1 | | 7/2002 | Hilaire et al. |
| 6,491,718 B1 | | 12/2002 | Ahmad |
| 6,527,799 B2 | | 3/2003 | Shanley |
| 6,540,774 B1 | | 4/2003 | Cox |
| 6,652,579 B1 | | 11/2003 | Cox et al. |
| 6,796,997 B1 | | 9/2004 | Penn et al. |
| 7,018,400 B2 | | 3/2006 | Lashinski et al. |
| 7,135,038 B1 | | 11/2006 | Limon |
| 7,316,710 B1 | * | 1/2008 | Cheng ............... A61F 2/91 623/1.15 |
| 2002/0002400 A1 | | 1/2002 | Drasler et al. |
| 2002/0058988 A1 | | 5/2002 | Fischell et al. |
| 2002/0058989 A1 | * | 5/2002 | Chen ............... A61F 2/915 623/1.15 |
| 2003/0083646 A1 | * | 5/2003 | Sirhan ............... A61F 2/91 604/891.1 |
| 2003/0125797 A1 | | 7/2003 | Chobotov et al. |
| 2004/0002750 A1 | * | 1/2004 | Majercak ............... A61F 2/91 623/1.11 |
| 2004/0204751 A1 | | 10/2004 | Fischell et al. |
| 2005/0119723 A1 | | 6/2005 | Peacock |
| 2005/0273156 A1 | | 12/2005 | Burgermeister et al. |
| 2006/0004435 A1 | | 1/2006 | Burgermeister et al. |
| 2006/0009836 A1 | | 1/2006 | Burgermeister et al. |
| 2006/0015173 A1 | | 1/2006 | Clifford et al. |
| 2006/0030930 A1 | | 2/2006 | Burgermeister |
| 2006/0079954 A1 | | 4/2006 | Burgermeister et al. |
| 2006/0085059 A1 | | 4/2006 | Ehrlinspiel et al. |
| 2006/0100695 A1 | | 5/2006 | Peacock et al. |
| 2006/0115512 A1 | | 6/2006 | Peacock et al. |
| 2006/0271161 A1 | | 11/2006 | Meyer et al. |
| 2008/0097579 A1 | | 4/2008 | Shanley et al. |
| 2008/0132995 A1 | * | 6/2008 | Burgermeister ......... A61F 2/915 623/1.15 |

FOREIGN PATENT DOCUMENTS

| | | |
|---|---|---|
| WO | WO-93/16479 | 8/1993 |
| WO | WO 2004/028571 | 4/2004 |
| WO | WO 2005/053766 | 6/2005 |
| WO | WO 2006/044147 | 4/2006 |
| WO | 2006/105192 | 10/2006 |
| WO | WO 2007/024484 | 3/2007 |

\* cited by examiner

FIG. 13
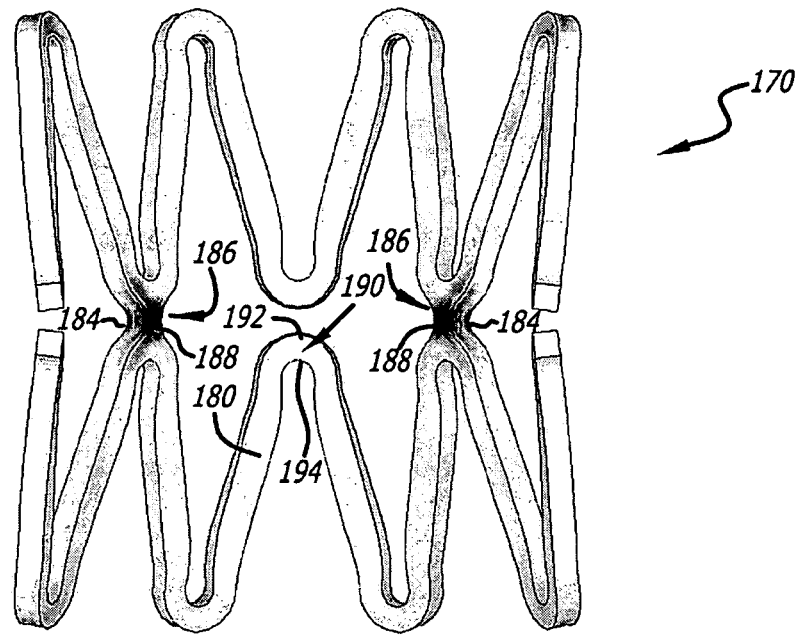
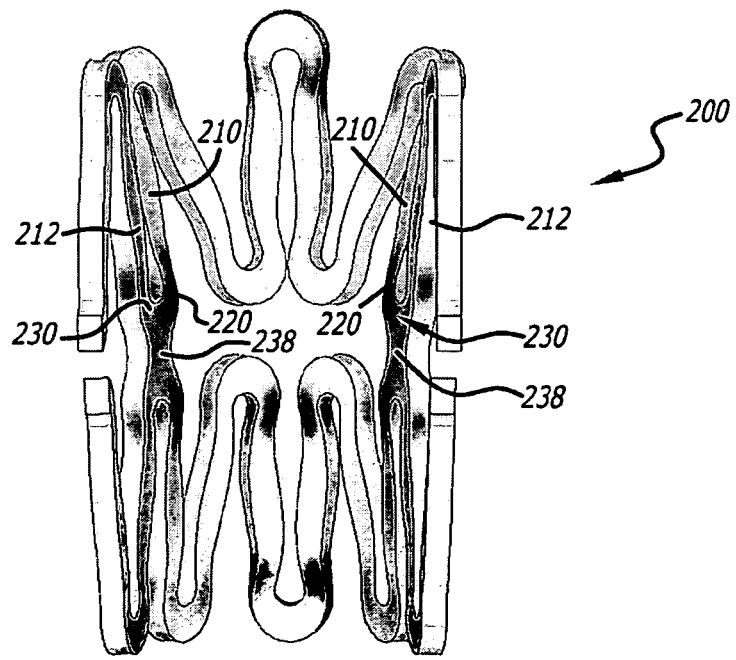
FIG. 14

IMPLANTABLE AND LUMEN-SUPPORTING STENTS AND RELATED METHODS OF MANUFACTURE AND USE

CROSS REFERENCE TO RELATED APPLICATIONS

The present application is a continuation of application Ser. No. 13/226,476, filed Sep. 6, 2011, now allowed, which is a continuation of application Ser. No. 11/943,527, filed Nov. 20, 2007, abandoned, which claims the benefit under 35 U.S.C. § 119(e) of U.S. Provisional Patent Application No. 60/981,433 filed Oct. 19, 2007, which are incorporated by reference herein in their entirety.

FIELD OF THE INVENTION

This invention relates to implantable medical devices. More specifically, the invention relates to implantable and lumen-supporting stents. Still more specifically, it relates to such stents for the treatment or inhibition of stenoses in coronary or peripheral vessels in humans.

BACKGROUND OF THE INVENTION

Cardiovascular disease, including atherosclerosis, is the leading cause of death in the United States. The medical community has developed a number of methods and devices for treating coronary heart disease, some of which are specifically designed to treat the complications resulting from atherosclerosis and other forms of coronary vessel narrowing.

An important development for treating atherosclerosis and other forms of vascular narrowing is percutaneous transluminal angioplasty, hereinafter referred to as "angioplasty." The objective of angioplasty is to enlarge the lumen of an affected vessel by radial hydraulic expansion. The procedure is accomplished by inflating a balloon within the narrowed lumen of the affected vessel. Radial expansion of the affected vessel occurs in several different dimensions, and is related to the nature of the plaque narrowing the lumen. Soft, fatty plaque deposits are flattened by the balloon, while hardened deposits are cracked and split to enlarge the lumen. The wall of the affected vessel itself is also stretched when the balloon is inflated.

Unfortunately, while the affected vessel can be enlarged thus improving blood flow, in some instances the vessel re-occludes chronically ("restenosis"), or closes down acutely ("abrupt reclosure"), negating the positive effect of the angioplasty procedure. Such restenosis or abrupt reclosure frequently necessitates repeat angioplasty or open heart surgery. While such restenosis or abrupt reclosure does not occur in the majority of cases, it occurs frequently enough that such complications comprise a significant percentage of the overall failures of the angioplasty procedure, for example, twenty-five to thirty-five percent of such failures.

To lessen the risk of restenosis and abrupt closure, various devices have been proposed for mechanically keeping the affected vessel open after completion of the angioplasty procedure. Such endoprostheses (generally referred to as "stents"), are typically inserted into the vessel, positioned across the lesion or stenosis, and then expanded to keep the passageway clear. The stent provides a scaffold which overcomes the natural tendency of the vessel walls of some patients to renarrow, thus maintaining the openness of the vessel and resulting blood flow.

While stents and stent applications of the type described have been found to work well in a number of patients, there is still room for improvement. First, various areas of the vasculature and different treatment sites call for stents with different characteristics. For example, a stent that must travel through a tortuous and highly-curved area of the vasculature to reach a particular treatment site would benefit from enhanced flexibility characteristics that are not necessarily needed in a stent used to treat an easily-accessible treatment site. Likewise, a stent that will be deployed at an area of a vessel that has a branch or bifurcation would benefit from flexibility characteristics not necessarily needed in a stent used to treat a relatively straight and uniform portion of a vessel.

Further, as stents are presently used, there can be an abrupt transition between the area of a vessel that is contacted by the stent (and thus receiving the benefits of the stent) and those portions of the vessel that are not. This abrupt transition between stented and unstented portions of a vessel can exacerbate the physiological trauma found at a treatment site. Thus, in some instances, a stent with characteristics that provide for a less abrupt transition between stented and unstented portions of a vessel may be advantageous.

Notwithstanding the foregoing, however, another frequent observation is that balloon expanded stents first deploy open under balloon inflation at their ends, with middle portion of the stent to follow. This is often referred to as "dog-boning" and has been suspected to result, in some cases, in increased trauma at end margins of treated areas. Because stent ends can deploy before middle stent regions and at lower balloon pressures, it would be considered advantageous to provide a new and improved stent that counteracts this with more uniform stent expansion. In particular cases where a stent may maintain a design with particularly beneficial lateral flexibility over its length, it would be desirable to also provide features at or adjacent the ends to result in a more uniform expansion over the length and including the stent ends.

Characteristics that result in low restenosis rates are also considered highly beneficial for most stent uses, such as for example for endovascular stents in particular. One such beneficial characteristic would be one that combats restenosis at locations along or adjacent the treatment site where restenosis is more frequently observed to occur, such as for example the area of the vessel nearest to the proximal (eg. "upstream" portion, as related to blood flow) end of the stent. Other such characteristics include for example enhanced tissue-device interface between the stent and tissue being implanted. Such enhancements may for example reduce trauma, reduce a restenotic or other undesired biological response to the implant, or otherwise benefit other aspects of the stent's intended use. In one particular regard, a pattern chosen for a stent scaffold, such as per undulating sinusoidal or "serpentine" strut-crown scaffolds most frequently used, may impact their capabilities in their use and/or with respect to outcomes. According to one more specific example, relative stiffnesses (including lateral, radial, or both) and geometries of crowns, struts, the connections or transitions between "segments" along a stent, and how these aspects relate to each other within an overall design, can have distinct impact on their in vivo use and outcomes.

It is also to be appreciated that certain stents, and their respective features related to their performance, are relatively small to the basic human observation skills such as sight and touch. The difference between features of one stent and another may appear very subtle, or not even readily noticeable, to initial visual or tactile observation. However, such otherwise subtle changes in or differences between such features may significantly impact the use of these devices, especially where intended for percutaneous transluminal delivery and chronic in vivo implantation within dynamic biological tissues such as blood vessels.

While endolumenal vascular stents have clearly become the most prominent type of stents used in medicine, it is also appreciated that stents may be, and have been, implanted in other regions of the body. For example, stents have been either proposed or used in other body lumens or spaces, such as without limitation within gastrointestinal tract, pulmonary system, urinary tract system, etc.

Various needs still remain for providing stents with improved features, including without limitation in order to beneficially improve various combinations of performance aspects such as trackability, visibility, expansion characteristics (e.g. uniformity of expansion, recoil, etc.), material fatigue and yield failure, tissue-device interface, surface coating adhesion and integrity, local drug delivery, and biological response and outcomes from their implantation.

SUMMARY OF THE INVENTION

One aspect of the present disclosure provides a stent system with an improved stent. According to one embodiment, the stent includes improved expansion characteristics. According to another embodiment, the stent includes improved lateral bending characteristics. In one particular embodiment, the stent undergoes lateral or radial deflection with strain distribution primarily at transition regions between struts and crown shoulders on opposite sides of crown peaks of the stent's filamental pattern. In another embodiment, the stent includes geometry along crown regions that differ from strut geometry, providing enhanced deflection characteristics in combination with enhanced characteristics along the strut, such as for example for drug delivery or visibility.

Another aspect of the present disclosure is an implantable medical stent system with a radially expandable stent comprising a filamental structure in a pattern surrounding a bore to form a substantially tubular wall along a length relative to a longitudinal axis. The filamental structure comprises at least one arcuate crown with a crown peak having a radius of curvature located along a reference axis, and first and second arcuate crown shoulders on first and second sides, respectively, of the reference axis. The filamental structure also comprises at least one pair of adjacent first and second elongated struts extending from the first and second crown shoulders, respectively.

The arcuate crown peak comprises at least one of: (a) a peak width that is greater than at least one of first and second shoulder widths along the first and second respective crown shoulders; (b) an outer radius of curvature about a first center that is offset from a second center of an inner radius of curvature; and (c) a radial expansion characteristic with a strain distribution that is substantially lower than along at least one of the first and second crown shoulders. According to a further mode, the crown peak comprises a combination of at least two of these particularly beneficial features. In a still further embodiment, the crown peak comprises each of these features.

Another aspect of the present disclosure is an implantable medical stent system with a radially expandable stent comprising a plurality of adjacent circumferential segments that comprise patterned filamental structures that surround a bore and are arranged in series along a length relative to a longitudinal axis to thereby form a substantially tubular wall along the length. Each pair of adjacent segments is connected by at least one of a plurality of connections between segments.

In certain further embodiments, at least one (and in further particular embodiments a majority of or each) connection comprises at least one of: (a) a longitudinal bending stiffness that is greater than a longitudinal bending stiffness along either adjacent segment such that upon an applied force of deflection lateral to the longitudinal axis the stent exhibits more longitudinal flexure within the segments than at the connections; and (b) a minimum width that is greater than a minimum width along a patterned filamental structure comprised by at least one of the adjacent segments.

According to a further embodiment, each connection comprises a combination or all of these features.

Another aspect of the present disclosure is an implantable medical stent system with a radially expandable stent comprising a filamental structure in a pattern forming a substantially tubular wall surrounding a bore along a length relative to a longitudinal axis, and with a plurality of adjacent alternating opposite facing arcuate crowns bridged by a plurality of elongated struts. Each crown comprises an arcuate crown peak with a radius of curvature located along a reference axis, and first and second arcuate crown shoulders on first and second opposite sides, respectively, of the reference axis. Each elongated strut extends over a length with an intermediate portion located between first and second end portions along the strut length, and also with inner and outer opposite edges relative to the reference axis. The first and second end portions of each strut are coupled to the first and second crown shoulders, respectively, of first and second adjacent opposite facing crowns, respectively.

According to certain further embodiments of this aspect, each strut comprises at least one of: (a) a maximum width along the intermediate portion that is greater than a width along the first and second end portions and that extends over less than one-half of the strut length; (b) a maximum width along the intermediate portion that is substantially greater than a radial thickness thereof; (c) a maximum width that is substantially greater than a width of the respectively adjacent crowns at either a crown shoulder or a crown peak thereof; (d) inner and outer radii along the inner and outer edges of the first end portion and that are substantially similar to outer and inner radii along the outer and inner edges of the second end portion, and (e) inner and outer substantially straight regions along the respective inner and outer opposite edges that are substantially offset such that a majority of each straight region does not overlap with the other straight region along the strut length and is associated with an arcuate region along the opposite edge.

According to a further embodiment, the struts comprise a combination of at least two of these features. In still further embodiments, the struts comprise a combination of three, four, and even each of these features providing further benefit in their combinations.

Another aspect of the present disclosure is an implantable medical stent system with a radially expandable stent comprising a filamental structure in a pattern surrounding a bore to form a substantially tubular wall along a length relative to a longitudinal axis. The filamental structure comprises at least one high strain region and at least one low strain region along the pattern. The filamental structure comprises a material strain distribution under deflection force of lateral bending or radial expansion relative to the longitudinal axis that is principally locally concentrated along the high strain region.

In another embodiment, the low strain region comprises at least one of (a) a width in a circumferential plane around the longitudinal axis that is substantially greater than a width of the high strain region along the longitudinal axis, (b) a width that is substantially greater than a radial thickness at the respective low strain region, and (c) a substantially increased radiopacity versus the high strain region.

According to further embodiments, the struts comprise a combination of two and even each of these individual features providing further benefit in their combinations.

Another aspect of the present disclosure is a method of deflecting a stent for at least one of radial expansion and lateral bending of the stent. This method includes applying a deflection force onto the stent for at least one of radial expansion and lateral bending of the stent. Further to this method, in response to the deflection force the stent undergoes a material strain that is principally locally distributed along at least one of: (a) a plurality of adjacent circumferential segments that surround a bore and are connected in series to form a substantially tubular wall along a longitudinal axis, and (b) a patterned filamental structure of the stent at a plurality of transition regions where a plurality of struts of the filamental structure extend between a plurality of crown shoulders of a plurality of opposite facing crowns of the filamental structure.

According to a further embodiment, the stent exhibits a combination of each of these characteristics. In another mode, the stent exhibits such combination of characteristics in each of radial expansion and lateral bending.

Various additional modes, embodiments, features, and variations are also contemplated with respect to these various aspects and modes, providing still further benefit and utility.

According to one such further embodiment, a system according to one or more the present aspects and embodiments includes a filamental structure pattern along a plurality of adjacent circumferential segments surrounding the bore and that are provided in series along the length. The filamental structure pattern of each segment comprises a plurality of arcuate crowns in alternating opposite facing orientations along a circumference of the segment surrounding the bore, and a plurality of pairs of struts, such that each pair of adjacent struts bridge the shoulders of one crown with a shoulder of each next adjacent opposite facing crown, respectively. Each adjacent pair of segments is connected by at least one connection.

In another embodiment of the system described above, the filamental pattern further comprises a plurality of adjacent circumferential segments surrounding the bore and that are provided in series along the length. The filamental structure pattern of each segment comprises a plurality of arcuate crowns with each crown having an arcuate crown peak with a radius of curvature located along a reference axis and first and second arcuate crown shoulders on first and second opposite sides, respectively, of the reference axis, the crowns being in alternative opposite facing orientations along a circumference of the segment surrounding the bore and comprising a plurality of pairs of adjacent struts bridging between opposite facing adjacent crowns in the respective segment such that each pair of adjacent struts bridge the shoulders of one crown with a shoulder of each next adjacent opposite facing crown, respectively. In another embodiment, each adjacent pair of segments is connected by at least one connection.

In another embodiment for a system such as described above, each of a plurality of arcuate crown peaks comprises a peak width, the first and second shoulders comprise first and second shoulder widths, and the peak width is greater than each of the first and second shoulder widths.

In another embodiment for a system such as described above, each of a plurality of arcuate crown peaks comprises an outer radius of curvature about a first center located along the reference axis, and an inner radius of curvature about a second center that is offset from the first center along the reference axis.

According to one embodiment, the first center of the inner radius of curvature of the crown peak is offset away from the crown peak on the reference axis relative to the second center of the outer radii of curvature of the crown peak, such that the second center is closer to the crown peak than the first center.

In another embodiment for a system such as described above, the strain distribution relative to each of a plurality of crowns during radial expansion of the stent comprises substantially higher strain along the first and second crown shoulders than along the crown peak.

In one embodiment, the strain distribution is substantially bifurcated and principally located along each of first and second transition regions between the first and second crown shoulders and first and second struts extending therefrom, respectively.

In another embodiment for a system such as described above, each of a plurality of arcuate crown peaks comprises a peak width that is greater than first and second shoulder widths along the first and second respective crown shoulders, an outer radius of curvature about a first center that is offset from a second center of an inner radius of curvature along the reference axis, and a radial expansion characteristic with a strain distribution that is substantially lower than along each of the first and second crown shoulders.

In another embodiment for a system such as described above, each of a plurality of connections between adjacent segments of a stent comprises a lateral bending stiffness that is greater than a lateral bending stiffness along at least one respectively adjacent segment, such that upon an applied force of deflection lateral to the longitudinal axis the stent undergoes more flexure within the segments than at the connections.

According to one embodiment, each connection comprises a lateral bending stiffness that is greater than a lateral bending stiffness of each respectively adjacent segment.

In another embodiment for a system such as described hereunder, each of a plurality of connections between adjacent segments of a stent comprises a minimum width that is greater than a minimum width along each adjacent segment.

According to one embodiment, the minimum width of each connection is greater than a maximum width of at least one of a crown or strut in at least one respectively adjacent segment. In another embodiment, the minimum width of each connection is greater than a maximum width of a majority of the crowns and struts in at least one respectively adjacent segment. In another embodiment, the minimum width of each connection is greater than a maximum width of all crowns and struts of at least one respectively adjacent segment. In another embodiment, the minimum width of each connection is greater than a maximum width along each respectively adjacent segment. In another embodiment, the minimum width of each connection is greater than a minimum width along a crown, strut, or transition region between crown and strut, in each respectively adjacent segment.

According to still another embodiment of the various aspects noted hereunder, each of a plurality of struts in a filamental structure of a stent comprises a maximum width along an intermediate portion thereof that is greater than along first and second end portions thereof that couple to first and second opposite facing crowns, and which maximum length of the intermediate portion extends along less than about one-half of the length of the strut.

According to one embodiment, the maximum width of the intermediate portion extends along less than about one-quarter of the length of the strut. In another embodiment, the maximum width of the intermediate portion is at a substantially discrete location along the strut and does not extend over a significant length of the strut. In still another embodiment, the first and second end portions of each strut comprises a tapering width reduction from the intermediate portion to first and second respectively coupled crown shoulders, such that the first and second end portions comprise first and second stiffness transition regions from the intermediate portion to the first and second adjacent crowns.

According to another further embodiment of the various system aspects described hereunder, each of a plurality of stent struts comprises a maximum width along an intermediate portion thereof that is substantially greater than a radial thickness thereof.

In one embodiment, the maximum width of the strut along the intermediate portion is at least about 25% greater than the radial thickness of the strut along the intermediate portion. In another embodiment, the maximum width of the strut along the intermediate portion is at least about 50% greater than the radial thickness of the strut along the intermediate portion. In further embodiments, the maximum width may be as much as 75% or greater than the radial thickness of the strut. However, in some applications, excessive width may provide detriment to certain performance related characteristics. Accordingly, as for such considerations in certain settings, further embodiments of the present disclosure include each such lower limit range noted above, but with its respective range being further limited at an upper limit that is equivalent to the other greater "at least" lower limits also noted.

In another embodiment, the maximum width of the strut along the intermediate portion is between about 0.0030 and 0.0050 inches, and the radial thickness of the strut along the intermediate portion is between about 0.0020 and about 0.0040 inches. In a further embodiment, the maximum width is between about 0.0035 and 0.0050 inches, with radial thickness between about 0.0030 and about 0.0040 inches.

These ranges (and other dimensional ranges provided hereunder) are considered of benefit in certain cardiovascular stenting applications for example, such as coronary stenting. Similarly adjusted ranges are contemplated, but with appropriately shifted magnitude of the respective limits with respect to either smaller or larger stents, or with more or fewer crowns, as would be apparent to one of ordinary skill.

According to still another embodiment, each of a plurality of stent struts comprises a maximum width that is substantially greater than a width of the respectively adjacent crowns at either a crown shoulder or a crown peak thereof.

In one embodiment, the maximum width of the strut along the intermediate portion is greater than a width of the respectively adjacent crowns at the respective crown peaks. In a further embodiment, the maximum width of the strut along the intermediate portion is at least about 20% greater than the width at the adjacent crown peaks. In a still further embodiment, it is at least 35% greater. In another embodiment, it is at least 50% greater. Again, in certain instances (and representing still further embodiments), such greater width may be limited at upper ends of ranges as well, such as similarly noted for other respective dimensional considerations above.

In another embodiment, the maximum width of the strut along the intermediate portion is greater than a width of at least one respectively adjacent crown at least at one crown shoulder of the crown.

In another embodiment, the maximum width of the strut along the intermediate portion is greater than a width at each crown shoulder.

In another embodiment, the maximum width of the strut along the intermediate portion is at least about 25% greater than a width at the crown shoulder.

In another embodiment of certain systems noted hereunder, each of a plurality of stent struts comprises a region of overlap between inner and outer opposite straight regions that is less than about one-half of the length of the strut. In one embodiment, the region of overlap is less than about one-fourth of the length of the strut. In a further embodiment, the region of overlap is less than about one-eighth of the length of the strut.

In still a further embodiment, each of a plurality of stent struts comprises each of: a maximum width along its intermediate portion that is greater than a width along its first and second end portions and that extends over less than about one-half of the strut length, and that is also substantially greater than a radial thickness thereof the intermediate portion, and that is also greater than a width of the respectively adjacent crowns at the crown shoulders thereof; inner and outer radii along the inner and outer edges of the first end portion and that are substantially similar to outer and inner radii along the outer and inner edges of the second end portion; and inner and outer substantially straight regions along the respective inner and outer opposite edges that are substantially offset such that a majority of each straight region does not overlap with the other straight region along the strut length and is associated with an arcuate region along the opposite edge.

In still a further embodiment, first and second crowns of adjacent opposite facing crowns in a stent segment are bridged by a strut. The first and second crowns comprise respective arcuate peaks with respective radii of curvature centered along first and second reference axes, respectively, and with each respective arcuate crown also comprising first and second arcuate shoulders located on first and second opposite respective sides of the respective reference axis. Each elongated strut extends over a length between first and second end portions that are coupled to first and second respective shoulders of the first and second crowns, respectively. Each elongated strut also comprises an inner edge and an outer edge along the length relative to the first reference axis. The inner edge along the first end portion comprises a first arcuate region extending over a first length with a first radius of curvature away from the first reference axis and toward the second reference axis. The inner edge along the second end portion comprises a second arcuate region extending over a second length with a second radius of curvature toward the first reference axis and away from the second reference axis. The outer edge along the first end portion comprises a third arcuate region extending over a third length with a third radius of curvature away from the first reference axis and toward the second reference axis. The outer edge along the second end portion comprises a fourth arcuate region extending over a fourth length with a fourth radius of curvature toward from the first reference axis and away from the second reference axis. The first and third arcuate regions differ with respect to at least one of their respective radii of curvature and length, the first and fourth arcuate regions are substantially similar with respect to at least one of their respective radii of curvature and length, and the second and third arcuate regions are substantially similar with respect to at least one of their respective radii of curvature and length.

According to another embodiment, each of a plurality of elongated stent struts extends over a length between first and second end portions that are coupled to and integral with first and second respective shoulders of first and second adjacent opposite facing crowns, respectively. Each elongated strut comprises an inner edge and an outer edge along the length relative to the reference axis of the first adjacent crown. The inner edge along the first end portion comprises a first arcuate region with a first radius of curvature away from the reference axis and that extends from the first crown shoulder to a first location along the strut. The outer edge along the first end portion comprises a second arcuate region with a second radius of curvature away from the reference axis and that extends from the first crown shoulder to a second location along the strut that is closer to the first crown shoulder than the first location. The outer edge further comprises a substantially straight edge region extending at least from the second location to the first location along the strut and that coincides at least in part with a portion of the first arcuate region along the inner edge.

According to still another embodiment, each of a plurality of adjacent interconnected stent segments comprises a first plurality of similarly oriented facing crowns that each faces and is aligned with a unique one of a second plurality of opposite oriented facing crowns, relative to the first plurality, of another adjacent segment. A plurality of the connections are located at each of a plurality of locations between each adjacent pair of segments along the length. Each of the plurality of connections at each location connects first and second opposite relative facing crowns of the first and second pluralities of the first and second adjacent segments, respectively.

In still another embodiment, a delivery system is coupled to the stent and is configured to deliver the stent to a location within a body of a patient and implant the stent at the location. In one embodiment, the stent is balloon expandable and the delivery system is a balloon catheter. In another embodiment, the stent is self-expandable and the delivery system comprises an outer retention sheath or tether system. In another embodiment, the delivery system comprises a guidewire. In another embodiment, the delivery system comprises an actuator to deploy the stent, e.g. such as an inflation device for balloon expansion.

In another embodiment, a bioactive agent is provided in a preparation configured for delivery into a patient and adapted to provide combination therapy with the stent implanted at a location within a body of the patient. According to one embodiment, the stent comprises a substrate material with a surface, a coating is located on the surface, and the bioactive agent is stored by and elutes from the coating at the location. In another embodiment, the stent comprises a plurality of discrete reservoirs within a metal scaffold filament, and the bioactive agent is housed within and elutes from the reservoirs at the location.

In another present embodiment, the stent comprises a filamental material that comprises a metal. In further embodiments, the metal may be for example stainless steel, nickel titanium alloy, or cobalt-chromium alloy. According to one still further metal alloy for such uses, a cobalt-chromium alloy is used that is of the L-605 cobalt-chromium type alloy.

In another embodiment, each of a plurality of connections between adjacent stent segments comprises a cross-over between portions of a continuous integral material corresponding with each adjacent segment.

In another embodiment, each of a plurality of connections between adjacent stent segments comprises a connector extending between portions of filamental material in each adjacent segment.

In another embodiment, each connection comprises a weld joint between portions of filamental material in each adjacent segment.

In another embodiment of the present method aspects presented hereunder, such method further includes applying a lateral deflection force for lateral bending, wherein in response to a lateral bending deflection force, the stent undergoes a material strain that is principally locally distributed along the plurality of adjacent circumferential segments.

In one embodiment, the material strain along the plurality of adjacent circumferential segments is principally distributed along a patterned filamental structure within the segments at a plurality of transition regions where a plurality of struts of the filamental structure extend between a plurality of crown shoulders of a plurality of opposite facing crowns of the filamental structure.

In another further method embodiment, the steps further include applying the deflection force onto the stent for radial expansion of the stent. In response to this deflection force, the stent undergoes a material strain that is principally locally distributed along a patterned filamental structure of the stent at a plurality of transition regions where a plurality of struts of the filamental structure extend between a plurality of crown shoulders of a plurality of opposite facing crowns of the filamental structure. In one embodiment, the principally locally distributed material strain along the patterned filamental structure is located within the plurality of adjacent connected segments.

It is to be appreciated that each of the various aspects, modes, embodiments, features, and variations noted above is considered to be independently valuable and beneficial without requiring necessary combination(s) with the others. However, it is also appreciated that such further combinations are also contemplated to provide still further benefits and value, and also within the scope of the present disclosure. Other aspects, modes, embodiments, features, and variations will be apparent to one of ordinary skill upon further review of the detailed embodiments set forth below, and furthermore with respect to those claims which are appended herewith.

BRIEF DESCRIPTION OF THE DRAWINGS

FIG. 13 shows a computer simulation of another representative portion of two adjacent segments of a similar stent model as that shown in FIG. 9, and modeled according to one particular construction sharing certain similar features with the stent embodiment illustrated in FIGS. 1A-D, although as subjected to a different lateral bending simulation under computer FEA, and shows shading to reflect varied levels of material strain along the modeled structure in the simulation.

FIG. 14 shows a computer simulation of another representative portion of two adjacent segments of a similar stent model as that shown in FIG. 10, and modeled according to one particular construction sharing certain similar features with the stent embodiment illustrated in FIGS. 2A-F, although as subjected to a different lateral bending simulation under computer FEA, and shows shading to reflect varied levels of material strain along the modeled structure in the simulation.

DETAILED DESCRIPTION OF THE INVENTION

Figure 1A:
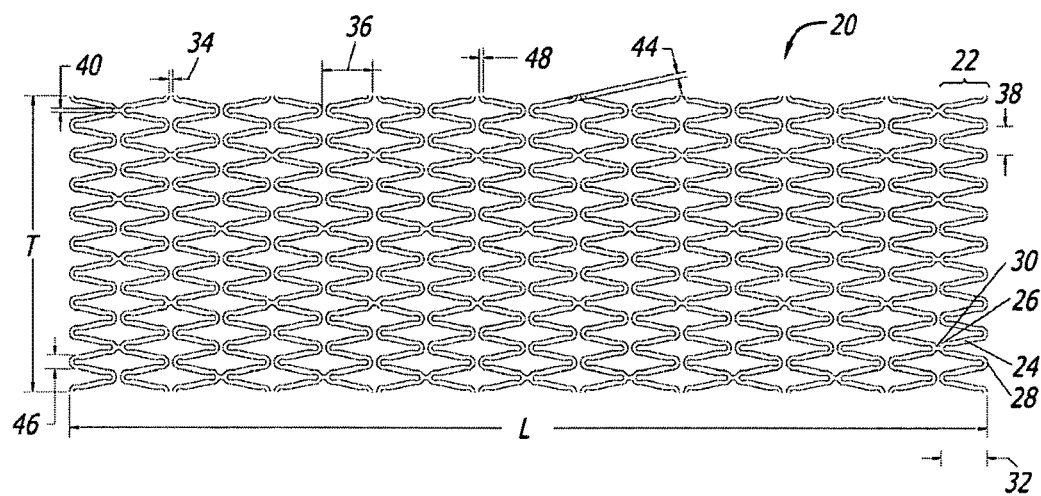
FIG. 1A shows a 2-D CAD drawing of one tubular stent of the present disclosure in longitudinally spliced and radially opened planar view.

The present invention provides methods and devices associated with certain stents that are considered to provide certain particular benefits in view of prior disclosures and devices previously used. Certain stents of the present disclosure are believed to present significant benefit in most "front-line" frequent intended uses, including most cases presenting specific challenges. Others include those which are individually and collectively useful at particular treatment sites requiring, or at least benefiting from, stents with particular characteristics. Certain of the present stents adopt certain specific characteristics considered of particular use in one or more unique circumstances. However, while certain such characteristics may be particularly attributed to one particular stent embodiment as herein shown and described, it is contemplated that various combinations between the present embodiments are also contemplated within the scope of the present disclosure though not specifically hereunder shown or described, as would be apparent to one of ordinary skill.

It is appreciated that, while a particular design feature or characteristic may vary between stents, such may also vary even within a stent itself, such as for example along the length of the stent. In one particular regard, stents of one significant type contemplated hereunder are most typically constructed of repeating or otherwise series of adjacent expandable scaffold "sections" along a length. These sections circumferentially surround a longitudinal bore around which they are expandable to maintain a patent lumen when implanted along a body lumen wall. Adjacent sections of stents are maintained in a particular spatial relationship relative to each other during use by crossovers (in which case the material between sections is continuous), connectors (discrete members connecting adjacent sections) or by weld or fusion points (hereinafter "weld points"). These terms are collectively referred to as "connections." Different characteristics along the length of a stent are created in accordance with certain teachings of the present disclosure by varying the number of connections between adjacent sections of a stent.

As used herein, the proximal and distal ends of a stent are to be interpreted as relative to each other and in relation to the distal end of the catheter that delivers the stent to a treatment site. Specifically, the distal end of the stent is closer to the distal end of the delivery catheter than the proximal end is.

Further to the particular present stent embodiments shown and described, these most frequently feature circumferential sinusoidal or serpentine patterns for each stent section. According to certain such embodiments, each section includes a circumferentially spaced series of proximal and distal "crowns" that include peaks of bends in the stent scaffold filament material. These are typically formed integral with struts that extend between and connect each distal crown to a proximal crown according to certain particular beneficial embodiments.

In general, a filament transitions from a strut section to a crown section (e.g. a crown portion begins) at a region where the radius of the bend begins. For example, in the case of a simple focal bend or elbow in a relatively constant sized filament (e.g. regarding one or both of width, thickness, etc. for example), the crown begins (e.g. following along the axis of a filament bridging between crowns) when the trajectory of the filament begins to curve or converge toward a crown "peak", which is defined as the inflection where the filament's trajectory reverses direction relative to the longitudinal axis of the stent. Moreover, certain crowns may also include more complex geometry than a simple focal elbow, yet nonetheless result in some fashion in a peak where the shaped filament reverses its longitudinal trajectory or direction. In particular, some crowns include multiple different radii of curvature at different regions. In one such particular approach, one or both of two converging struts on either side of a crown may be radiused at one or more locations to instead provide a transitionary divergence between the struts over a transition region prior to inflecting again with another radiused curvature or bend to again converge to ultimately meet along what is typically a continuous filamental pattern through the crown region. This multiple radiused crown pattern provides one example of an "enlarged" crown, with two opposite shoulders providing the transition regions with the two adjacent struts coupled to the crown, and with adjacent struts diverging to an increased width across the shoulders between the struts and the crown peak.

Of particular benefit in further embodiments, these struts and crowns are formed integrally from one continuous piece of material. In still further beneficial embodiments, the overall stent including struts, crowns, and connections is formed from one integral piece of material, such as for example as a laser cut or etched tube or other piece of workpiece material processed into the patterned tubular structure.

Stents constructed according to the present disclosure may be made from various different types of materials as may be apparent by one of ordinary skill. However, certain particular examples considered to provide particularly beneficial use include stainless steel, cobalt chromium, and nickel-titanium alloys (the former two being generally balloon expandable, the latter being generally self-expanding either by superelastic material recovery or heat induced shape memory). Of the balloon expandable type, a cobalt-chromium of the L-605 alloy type has been observed to provide particular benefit, e.g. as provided by experiments conducted with physical embodiments, e.g. as provided in preclinical implant studies in the Examples of this disclosure. However, as noted, other alloys may be chosen to suit a particular purpose or intended use. In addition, as noted, stents per the present embodiments may be either balloon expandable, or self-expandable.

The specific detailed embodiments herein shown and described are generally described in terms of balloon expandable types for purpose of providing a complete and thorough illustration of such family, which is generally prevalent in coronary interventions (though also predominant or at least a present approach in other areas of the body). The balloon expandable type of stent obviously includes a balloon catheter type of delivery system, which typically tracks over a guidewire to a location for stenting (though some approaches may integrate a guidewire either in fixed fashion or limited relative motion with the catheter). The self-expanding type will often employ an outer retention sheath that holds the stent in radially collapsed deflected condition from a memory condition that is radially expanded. By removing the outer sheath, the stent deploys under material memory recovery for "self-expansion." It is to be appreciated that in either case, balloon dilatation may be performed adjunctively to stenting, e.g. either before, during, or after stent implantation. In addition, the present stent embodiments may also be combined with other therapies though with intended synergistic combination effect. One such example is atherectomy of a lesion adjunctive to stenting, and/or use of embolic filters in combination with stenting, and/or certain diagnostic or imaging devices or methods such as interventional vascular ultrasound (IVUS) or angiography.

For purpose of the present embodiments as shown and described variously by reference to the Figures, adjacent stent segments or sections are given reference numbers in sequential order starting at 1 on the left side of the drawings shown, and then increasing by integers referencing each next adjacent section to the right in the Figure. Certain stent designs shown include "peak-to-peak" (also referred to as "crown-to-crown") designs, wherein a distal facing crown peak of one section faces or confronts a proximal facing crown peak of the adjacent section, though a gap or space may remain between the facing peaks. For purposes of identifying where crossovers or connections are provided at these confronting peak areas, a position along the length of the stent (eg. interface between two sections) and location circumferentially along that position (eg. peak-to-peak interface) are given numbered reference designations by certain conventions shared among the Figures as follows.

The designations for sequential stent segments or sections start at the first section designated as 1 on the left in a Figure as section 1, whereas the first designated position 1 for cross-overs or connections is the first section-section interface from the left, each designation increasing by sequential integers toward the right in the respective Figure.

The convention for designating the relative location of crowns in a particular segment or section begins at the first crown designated as 1 at the uppermost area at the top of the respective Figure, and increasing by sequential integers at each next crown peak moving downward toward the bottom of the drawing. Where a Figure shows a tubular stent drawn in planar view (eg. CAD drawings, such as FIGS. 1A, 2A, 3A, 4, 5, 6A, and 7A, that are planar representing longitudinal splice along the stent that is filleted open on the page), the tubular result is provided by folding the planar view back together around the longitudinal axis with the top lateral edge of the drawing meeting the bottom lateral edge of the drawing. The transverse height transverse to the longitudinal axis in such planar views thus represents the circumference of the tubular stent. Such planar stent illustrations at certain sections will bisect certain crown peaks such that one half of the crown peak is at the upper edge and other half is at the lower edge of the drawing. Where this occurs at a confronting crown peak area, the convention reference numbering begins at the top of the drawing where the confronting crown peaks are shown in bisected form.

Accordingly, for serpentine designs as described, the top most crown is designated as location 1, the next crown downward (typically pointing in opposite direction to the crown at location 1) is designated as location 2. Further to this convention, each distal facing crown in a segment is thus separated from the next distal facing crown bin the same segment y two integers, as the intervening integer designation is given to the opposite facing crown between them, which progresses similarly for proximal facing crowns.

For further understanding, an "X crown" description provided for a particular stent embodiment hereunder represents X number of full cycles of an undulating pattern per segment, thus X crowns in a particular direction per segment, eg. for a sinusoidal pattern for example. According to this convention, a stent described as an "X crown" design thus actually includes 2X crowns total, or X crowns in each of two directions, over the entire undulating pattern of distal and proximal facing crowns in a segment. For still further illustration, a "10 crown" design designates 10 full cycles of undulating pattern per segment, such as 10 proximal and 10 distal facing crowns for 20 total crowns in a segment.

The present invention is considered of particular benefit when applied according to the teachings of the more particular embodiments herein shown and described. However, the various aspects, modes, embodiments, and features herein presented are also considered applicable to these and other previously disclosed or known stent designs to the extent such may be readily modified or adapted consistent with the present embodiments according to one of ordinary skill upon review of this disclosure. U.S. Pat. Nos. 5,292,331 and 5,135,536 to Boneau and Hilstead respectively, and the references cited therein, are herein incorporated in their entirety by reference hereto. It will be readily apparent from the following discussion of several exemplary designs how the various beneficial aspects of the present disclosure can be applied broadly across a wide spectrum of such other aspects of stent constructions, including in ways that provide beneficial results not otherwise readily apparent or to be expected without the benefit of the present disclosure.

The sections of the stents of the present invention can have more or less undulations within a section or more or less sections overall than provided by the specific illustrative examples herein shown. However, it is nonetheless appreciated that various of the detailed features, and their combinations, as herein specifically shown are considered to provide particular benefit, and in any case sufficiently exemplify certain broader aspects herein contemplated as present invention.

As used herein, "open designs" have fewer connections between adjacent sections and thus create a more flexible area of the stent. Closed designs of the present disclosure have more connections between adjacent sections and thus create a less flexible, more supportive area of the stent. Thus, the number of connections is varied to create particular characteristics at different portions of the stent. The terms "open" and "closed" are to be interpreted as relative to each other within a particular stent, unless otherwise specifically stated. Thus, a portion of a stent that is described as closed in one stent may be "open" when compared to a more closed portion of a different stent. Such reference labels are thus not appropriately to be applied as between different stents, unless otherwise so stated, and thus the exemplary "closed" portion of a stent as typically used hereunder is defined as such when compared to other portions of the same stent.

Further, a transition from open to closed or vice versa need not be uniform as progressing along the length of the stent, but instead can consist of progressions of a more general nature. For example, in a stent comprising a maximum of six crossovers between each section, a progression from open to closed may progress as (in number of connectors between adjacent sections): 1, 1, 2, 2, 3, 3, 4, 4, 5, 5, 6, 6. This progression could also include, however, progressions such as, without limitation, 1, 2, 1, 3, 2, 4, 3, 4, 5, 6, 5, 6 or 2, 1, 3, 1, 2, 4, 3, 5, 6, 4, 6, 5. Phrases such as "connector position" or "crossover position" refer to the portions of a stent between sections or at the intersection of sections wherein there is an opportunity to provide or modify the number of connections.

Notwithstanding the foregoing, certain particularly beneficial stents of the present disclosure are variously shown and described in more detail by reference to the illustrative Figures herein shown as follows. While individual Figures and series of related Figures will be further described in specific detail further below, it is to be appreciated that certain specific variations of numbers and lengths or amplitudes of stent sections, number and locations of crowns per section, and number and locations of crossovers between sections are represented among the Figures on the whole.

More specifically, FIGS. 1A, 2A, 3A, 4, 5, 6A, and 7A are respective computer aided design (CAD) drawings of stents that represent certain specific embodiments of the present disclosure. The particular number of sections, number of crowns per section, and number and location of crossovers at each section-section position along the stents for each of these particular embodiments are shown in Table 1. In this regard, the term "position" reflects the section-section interface along the length of the stent where the respective cross-over(s) are identified, and the term "location" reflects the designated peak region where the crossovers are located at a given position. The number of crossovers at a position are shown first, whereas their respective locations at that position are shown parenthetically in Table 1.

As should be apparent from Table 1, certain particular features and combinations thereof are herein contemplated, including without limitation with respect to, for example: number of sections along a stent length, number of crowns per section, and number and locations of cross-overs or connections between sections at each section-section position. While certain of these particular embodiments are considered of particular benefit, it is nonetheless still to be appreciated that certain broad aspects of the present disclosure need not be necessarily limited to such specific features in order to still provide beneficial uses. A variety of different designs can provide suitable further embodiments of such broad aspects of the present disclosure, though not specifically shown here in the detailed embodiments.

For example, as a guideline to certain particular modes herein presented, in order to determine whether a particular stent adopts a closed-open-closed design, as elsewhere herein further described, the stent could be divided into three equal portions (i.e. same number of crossover positions). If the number of crossovers, connectors or weld points is counted in each portion, each closed end portion should individually have at least one more crossover, connector or weld point than the middle open portion. The closed end portions need not have the same number of crossovers, connectors or weld points. Alternatively, to determine if a stent is a closed-open-closed design, a stent could be divided into two end portions, whose number of crossover positions together is the same or different from the number of crossover positions of the middle open portion. With this method, regardless of its size, each closed end portion should have a greater percentage of connections compared to the percentage of connections found within the open middle portion. Percentage refers to the actual number of connections compared to the spaces for possible connections.

As stated elsewhere hereunder, stents adopting a closed-open-closed design are considered particularly useful for treatment areas that include a vessel branch or bifurcation, assuming the open middle portion is sufficiently "open" to provide the various benefits considered helpful to such applications. In one regard, the open middle portion provides for greater flexibility at the irregular shape of the branch or bifurcation. If the open middle portion gates a side branch or one side of a vessel bifurcation, the open configuration may also be opened further through balloon inflation to promote blood flow to the gated vessel. In addition to having an open middle portion, in one embodiment, this stent design can also include longer stent sections in the middle of the stent which could increase the flexibility of this portion of the stent further. Finally, a second stent could be deployed through the open middle portion into the second vessel stemming from the branch or bifurcation. The closed ends of this stent design may also provide additional support for the vessel on both sides of the flexible and open center.

However, it is also to be appreciated that a "closed-open-closed" design, to the extent described as such relative to its own sections, may provide particular performance benefits beyond those just described, especially when compared instead to stents of other designs. In one particular regard, a stent that is considered "closed-open-closed" because its ends have more connections or cross-overs than its middle section may nonetheless still have greater flexibility at its ends, and perhaps improved trackability, when compared against another stent which is otherwise considered an "open-closed-open" design. This is the case, for example, when a first "closed-open-closed" stent, having three cross-overs between the terminal sections at its proximal and distal ends versus two cross-overs between the middle sections, is compared against a second "open-closed-open" stent design, having for example four cross-overs between terminal sections at its proximal and distal ends versus six cross-overs between its middle sections. Even though the second open-closed-open design has fewer crossovers at its ends than its middle portion, its ends nonetheless have more cross-overs and thus more closed-cell design than the ends of the first stent otherwise labeled "closed-open-closed". Thus, assuming all other design features of the stents being equivalent in this example, other than their respective cross-over numbers and locations, the first stent may be more flexible, and more trackable, at its ends than the second.

Further detailed aspects of the present embodiments shown in the Figures are described as follows.

FIG. 1A shows a stent 20 which is tubular (but shown in planar view) with a series of n=18 sections 22 arranged in series along a length L relative to a longitudinal axis. A transverse axis T represents the circumference of the stent 20 for the degree of expansion shown, represents circumference if upper and lower edges of the Figure were brought together to configure stent 20 shown in planar view instead into a tube. The sections or segments 22 each have an undulating pattern with a "10 crown" design per section, meaning for example having 10 proximal facing crowns, and 10 distal facing crowns as "valleys" between the first proximal crowns. A full or 360 degree cycle 38 of the undulating crown pattern shown represents a distance between similarly situated peaks (eg. two adjacent distal facing peaks along the axis T of the segment), whereas a ½ or 180 degree cycle would reflect a portion between adjacent proximal and distal peaks in the pattern. Extending between the proximal and distal facing crowns are struts, such as for example at struts 24 between opposite facing crowns 26, 28 as shown in FIG. 1A. The overall pattern for the interconnected network of scaffold material shown for stent 20 further includes cross-overs 30 between certain peak-to-peak interfaces between adjacent segments, as described hereunder in further detail by reference to FIG. 1A in Table 1. The overall segment amplitude 32 is shown between opposite facing peaks of adjacent proximal and distal crowns 26, 28. Except where crossovers are located, gaps 34 are shown between facing peaks of adjacent segments. This allows for a range of compression between adjacent segments during flexure of the overall stent 20, such as when crimped onto a balloon and tracked through bends over a guidewire, for example. According to this consideration, a complete segment length 36 is considered the amplitude 32 of the segment crown-crown distance plus this gap 34 to the next adjacent segment or section.

In addition, FIG. 1A shows the segment crowns to include a crown width 46, which though shown in one condition may change its value over ranges of radial stent expansion and as designated in the illustration by the magnitude of its circumference depicted in planar sectioned view along transverse axis T. The cross-over areas 30 are also shown to include a width 40. It is to be appreciated that changes in the number, relative locations, and widths 40 of these crossovers 30 may affect the performance of stent 20, as will variations of these features as taken in combination with other features provided by the stent. This will be further developed with respect to other embodiments below.

Figure 1B:
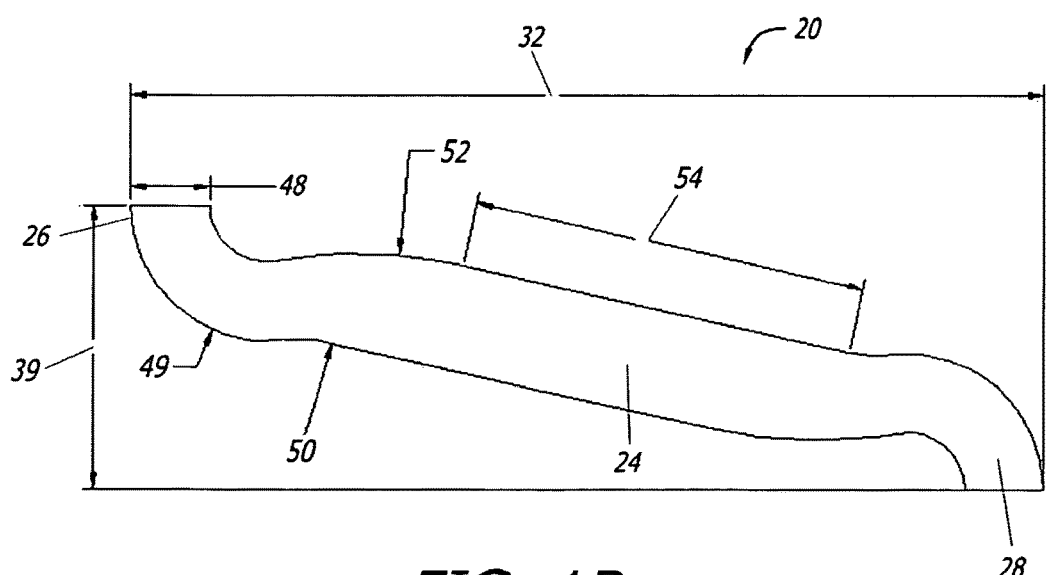
FIG. 1B shows an exploded top view of certain strut and crown detail of the stent shown in FIG. 1A.

FIG. 1B shows further detail of an exploded ½ cycle portion of a stent segment as follows. According to this detail shown, varied widths across the scaffold filament are shown, for example at width 48 at the peaks of crown 26 (and similar at opposite facing adjacent crown 28 as shown), and at strut 24.

Moreover, a transition region of varied width exists between the relatively constant width portion of strut 24, with variously located radii along opposite top and bottom edges bordering the filament (relative to the drawing on the page), such as shown at one radiused region 52 on one edge surface (toward top of page in drawing) and second radiused region 50 on the opposite edge surface. The locations of these radiused regions 50, 52 are slightly varied along the filament, and in such a manner at each end (right and left on page), such that a relatively constant straight portion along one edge of the filament at strut 24 is provided on each upper and lower edge, but are slightly staggered along the strut 24. This is shown for example at region 54 which is relatively constant straight at one edge of the strut over the distance shown, and whereas the relatively constant straight region opposite that edge may have substantially similar distance but is staggered to terminate about at 50 where the respective radiused region at that edge begins. In addition, it is apparent in FIG. 1B that the radii along the strut-crown transition region have centers of curvatures that, while at different locations, are located in a similar direction relative to the stent (eg. the curves are in a similar direction, though of different magnitudes and centers). These radii of curvature are in different direction (eg. outward) relative to the radius of curvature of the outer and inner edges of crown 26, such as shown for example at outer crown radius 49.

According to this arrangement shown in FIG. 1B and just described, the filament width has a desirable transition of mechanical properties as the strut 24 transitions into the respective crowns 26, 28 at either of its ends. Among other benefits, this particular transition arrangement provides for a transitioning stiffness in the transverse or circumferential plane T for controlled distribution of strain during radial compression or expansion of the respective stent 20. Additional benefit is also provided via certain enhanced flexibility provided at the transition region during lateral bending of the stent, such as for example when it is tracked through bends when compressed or "rolled down" during delivery, or through a range of mechanical bending that may be experienced when expanded and implanted.

Figure 1C:
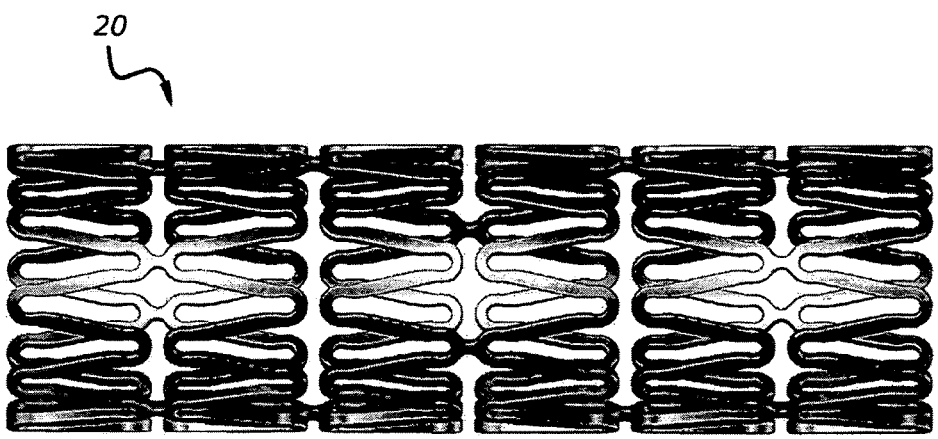
FIG. 1C shows a 3-D CAD illustration in side view of the stent shown in FIGS. 1A and 1B.
Figure 1D:
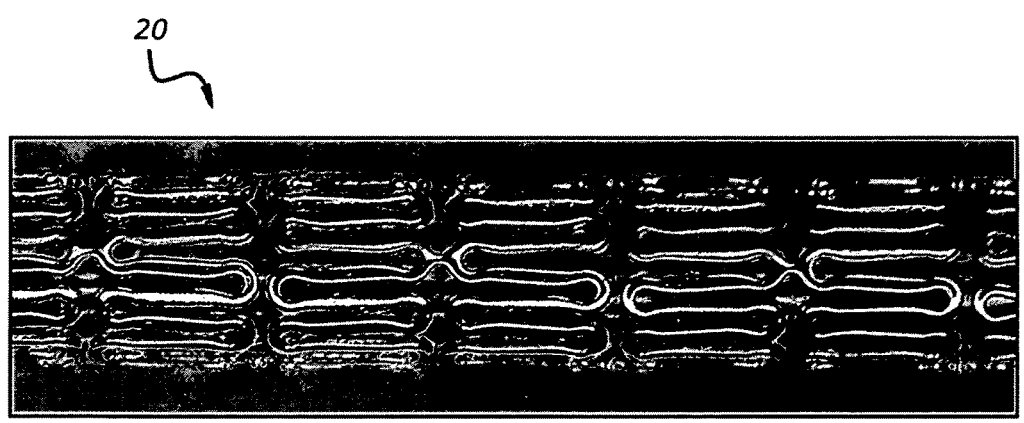
FIG. 1D shows a photograph in side view of a portion of a stent constructed to include similar features to the stent shown in FIGS. 1A-C.

For further illustration of a stent assembly such as just described by reference to the CAD animations shown in FIGS. 1A-B, FIG. 1C shows a CAD animation of stent 20 as simulated in 3-Dimensional tubular form. The condition for stent 20 shown in FIG. 1C is simulated to represent the overall structure as it would generally appear if "as cut" from a solid tube. For still further illustration, FIG. 1D shows a picture of an actual commercial embodiment example for a stent 20 incorporating similar features as those shown and described by reference to FIGS. 1A-C. In this particular picture, the stent is cut from a cobalt-chromium alloy tube, and subsequently electropolished.

The illustrative embodiment just described by reference to FIGS. 1A-D may be constructed of varied materials, and with varied particular dimensions, without departing from the broad aspects herein contemplated. However, for purpose of illustration, one particular construction exemplified by the physical embodiment shown in FIG. 1D is considered suitable, and of particular benefit, as follows. The stent intended to have 10 crowns/segment, 18 segments total, and about 1.0 mm segment length as illustrated for the current embodiment, is cut from cobalt-chromium alloy tubing. A cobalt-chromium tubing having "L605" alloy characteristics, 0.073 inch O.D./0.065 inch I.D. is used according to the present example. The laser cutting is conducted according to typical, suitable equipment and techniques, following two-dimensional CAD drawing provide, such as is shown in FIGS. 1A and 1B, and to achieve about the following dimensions by reference to those drawings (inches; post-cutting, but before post-processing such as electropolishing): overall length L=0.7170; transverse circumference T: 0.2300; crown overall width 46: 0.0110; crown-to-crown inter-segment spacing 34: 0.0030; segment amplitude (including spacing) 36: 0.0400; crown-to-crown period distance 0.0230; maximum strut width (at constant width portion) 54: 0.0042; length of constant straight edge section of strut 54: 0.0160; crown peak filament width 48: 0.0032; radius 50: 0.0055; radius 52: 0.0200; radius 49: 0.0055.

After cutting a stent as just described, it is subsequently treated in standard fashion, including electropolishing, etc. A post-processing stent filament thickness in the radial plane of between about 0.0025 inch to about 0.0031 inch thick is believed to provide particular benefit in the overall design. Such a stent is then prepared for integration together with a delivery assembly (eg. crimping onto a balloon), packaging, sterilization, shipping, and for subsequent use.

While the embodiment just shown and described by reference to FIGS. 1A-D is considered to provide certain particular benefits, FIGS. 2A-E show various illustrations representing a stent 70 providing a further embodiment of the present disclosure, and considered to add certain particular value-added beneficial improvements over previously disclosed designs.

Figure 2A:
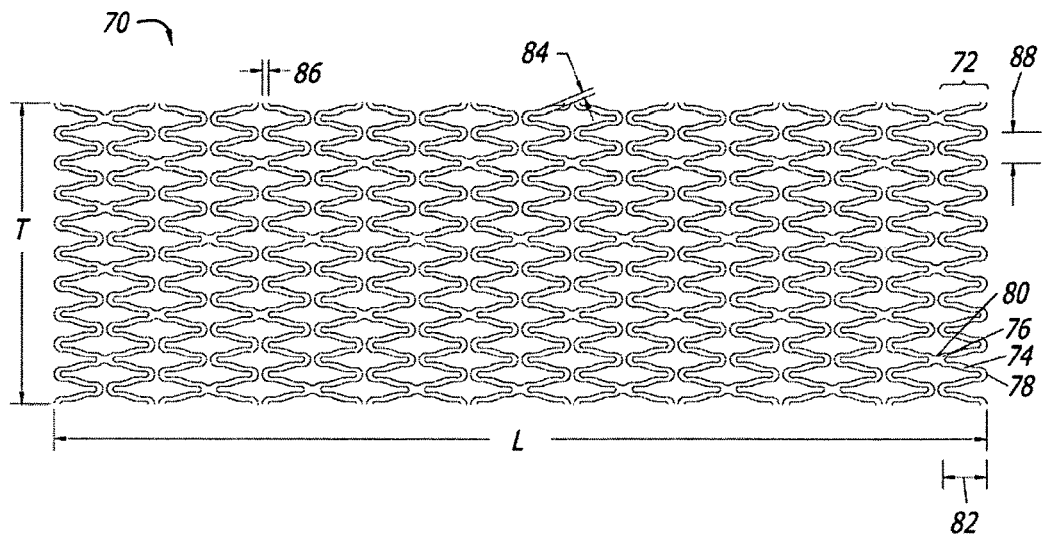
FIG. 2A shows a 2-D CAD drawing of another tubular stent of the present disclosure in longitudinally spliced and radially opened planar view.

More specifically, as shown in FIG. 2A, stent 70 shares certain features with stent 20 of FIGS. 1A-D, namely a "10 crown" design of 18 segments 72 over a length L, and of similar circumference along transverse axis T. Each segment 72 includes an undulating peak-valley-peak design bridged by struts, such as shown at strut 74 between opposite facing crowns 76, 78. Each segment has a peak-peak amplitude 82, with a period 88 between adjacent similarly oriented peaks. The respective central strut width is shown at 84, with primary peak width shown at 86, in FIG. 2A. However, it is noted that the filament width according to the present embodiment varies in certain particular regards considered to provide certain particular benefits, as further herein described by reference to finer details of such features, such as by reference to FIGS. 2B-C.

Figure 2B:
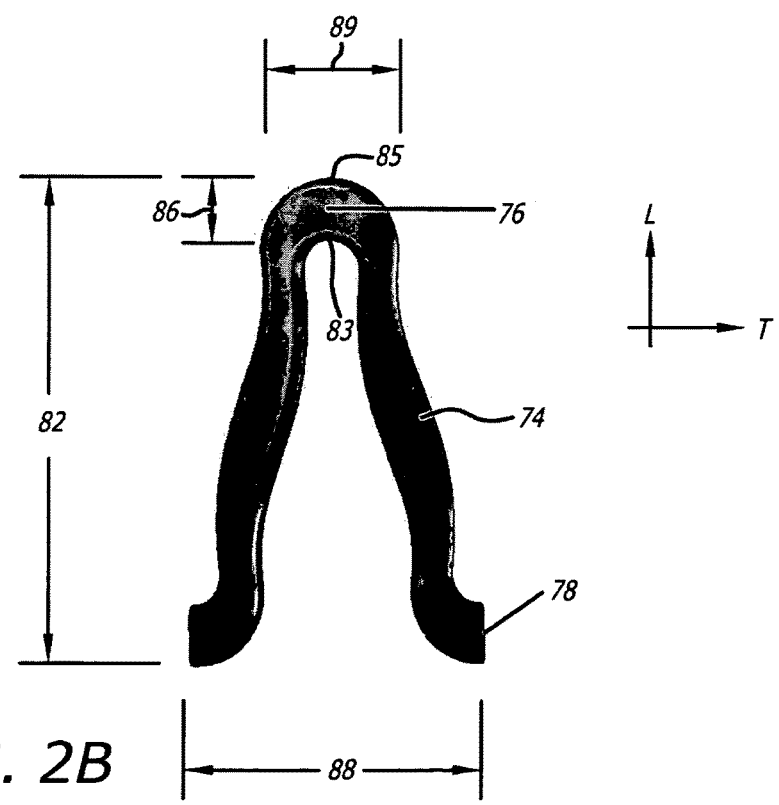
FIG. 2B shows a 3-D CAD drawing of an exploded top view of certain strut and crown detail of a full crown-crown cycle along a segment of the stent shown in FIG. 2A.
Figure 2C:
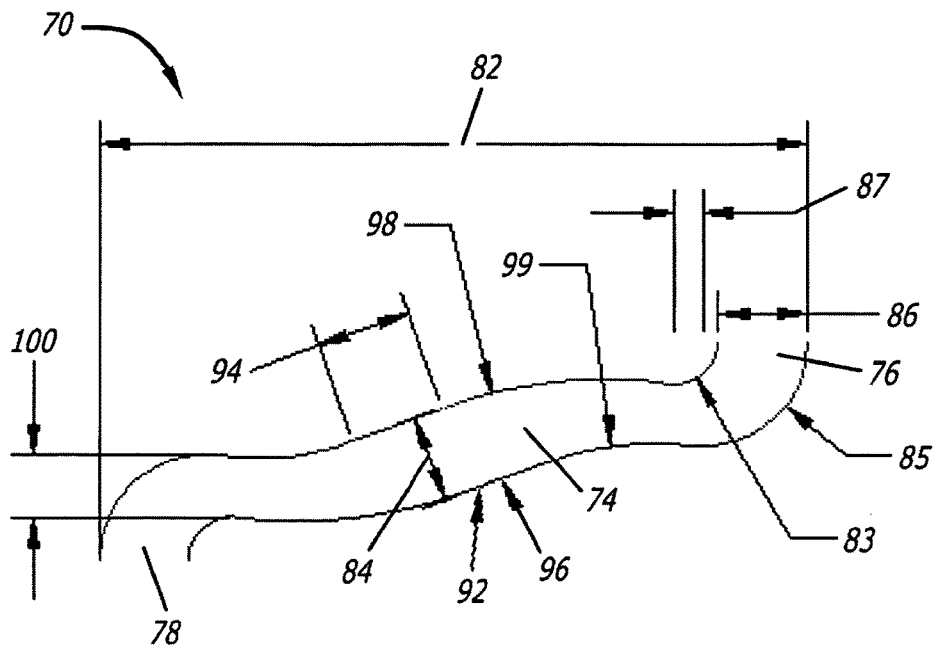
FIG. 2C shows an exploded top view of a 2-D CAD drawing of certain of the strut and crown detail of a half crown-crown cycle along the stent shown in FIGS. 2A-B.

FIGS. 2B-C provide exploded views of certain finer detail regarding the strut and crown features of stent 70, and which vary in certain regards from prior stents previously disclosed. In one particular regard, the use of radiused edges is more extensive, and thus a transitioning of filament geometry between struts and crowns is more exaggerated (with area of constant strut width conversely much more abbreviated), in the embodiment of stent 70 featured in FIGS. 2A-E versus prior disclosures or embodiments above. More specifically, radiused edges 98, 99, while still slightly staggered in a similar manner described by reference to FIG. 1B, extend over a longer extended region along the filament. As a result of extended radiused regions of strut-crown transition, the opposite edges 96, 98 strut 74 feature constant straight regions 92, 94 that are significantly shorter than in prior designs (including vs. stent 20 in FIGS. 1A-D). The region of overlap between these constant surfaces 92, 94 also spans very little of the distance along strut 74 between opposite facing crowns. As a result, stent 70 features a substantially abbreviated region of constant width along the respective strut 74, shown at width 84 (which may approach zero in certain further embodiments), with tapering transition along the radiused edges 98, 99 toward a minimum filament width 100 at the transition region approaching the respective crown.

This arrangement results in several highly desirable characteristics considered to enhance certain performance aspects of the respective stent. In one regard, a desirable distribution of stress and strain is experienced by virtue of the various tapers and transition region. By providing such improved transitioning, stent performance may be enhanced, including where certain trade-offs are frequently encountered, such as for example with regards to lateral flexibility and radial strength. Moreover, enhanced distribution of stress/strain during expansion and wear is considered a distinct benefit, including for example and in particular in setting of coated stents, such as drug eluting stents. In this latter regard, more typical conventional designs that distribute expansion strain across one focal crown peak region have been observed to result in compromised coating integrity. The current embodiment provides for a bifurcation of that strain to the two tapered transition regions at the crown shoulders for beneficially modified distribution of material strain from flexure or expansion. This is considered to present a particular enhancement for maintaining surface coating integrity. Accordingly, the present embodiments further contemplate inclusion of various surface coatings on the stent, and drug elution therefrom.

The present embodiment also features a particular crown design also considered to provide particular benefit, including in particular combination with other features provided by the embodiment. More specifically, as shown in FIGS. 2B-C, Crown 76 includes an inner radius 83 that is less than outer radius 85. Spacing 87 shown in FIG. 2C represents the separation between centers of outer radius 85 (located at end of line on right side of spacing in the Figure) and inner radius 83 (located at end of line on left side of spacing in the figure). The crown is generally defined as the arcuate region between inflection points from these inner and outer crown radii 83, 85 and transition region radii 98, 99. As a result of the overall geometry of such crowns, the largest width portion 86 of the crown region is at the peak (such as shown by location of reference arrows for the radii 83, 89 in FIG. 2B). The crown width transitions from this maximum width at the peak to gradually narrowing width toward the sides of the crown and into the transition region of narrowed width 100. This crown geometry is considered to provide certain further distinct benefits with respect to certain particular stent performance characteristics, including in particular with respect to stress/strain distribution along the stent and resulting mechanical characteristics during circumferential deformation, such as during radial crimping for delivery and radial expansion for implantation. This is further illustrated elsewhere in the present disclosure and by favorable comparison against other exemplary stents previously introduced and having experienced substantial commercialization and clinical use.

Certain beneficial features of the present embodiment shown in FIG. 2A are thus herein shown and described with respect to certain strut and crown details of the embodiment, such as for example as just illustrated above by reference to FIGS. 2B-C. However, other benefits are also provided by the present embodiment, as further shown and described by reference to FIGS. 2D-F as follows.

Figure 2D:
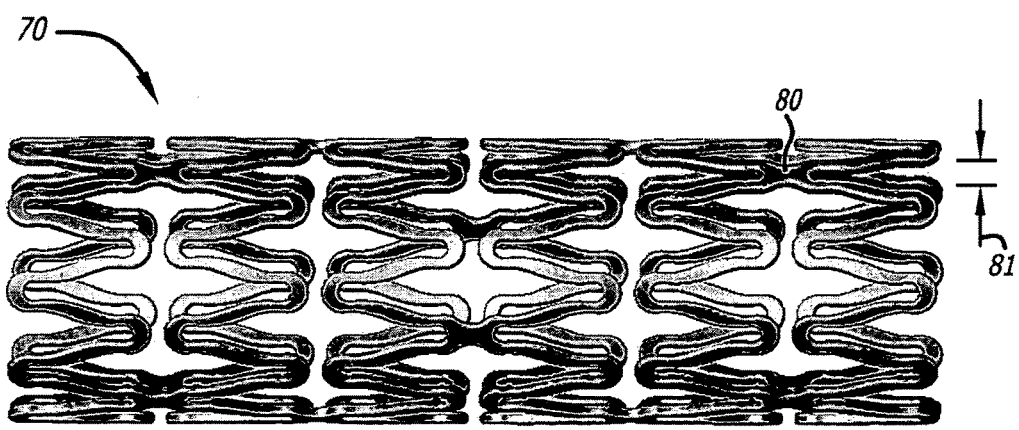
FIG. 2D shows a 3-D CAD illustration in side view of a stent shown in FIGS. 2A and 2C.
Figure 2E:
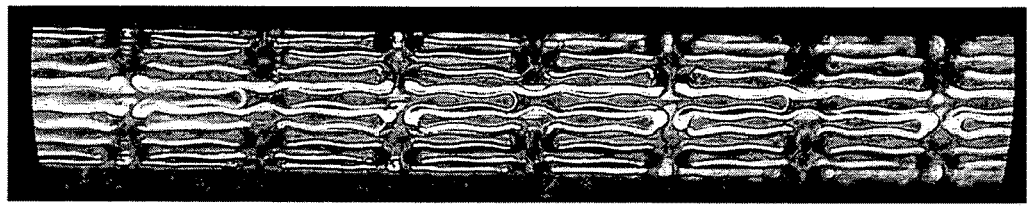
FIGS. 2E-F show photographs in side view at different respective magnifications of certain portions of a stent actually constructed to include similar features to the stent illustrated in FIGS. 2A-D.
Figure 2F:
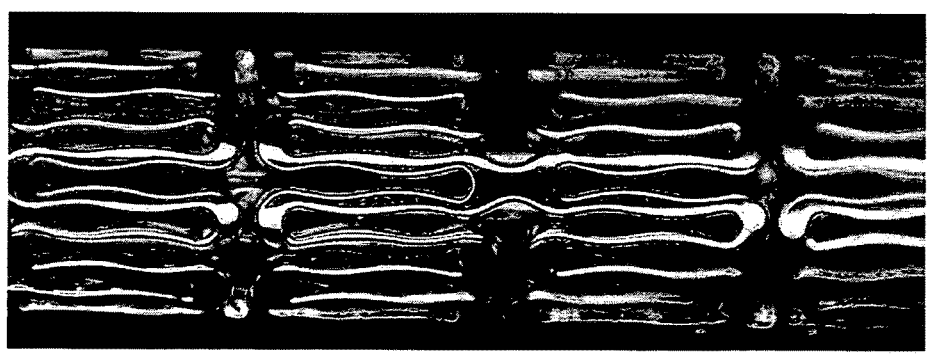

In particular, as shown in FIG. 2D (and by further reference to similarly constructed commercial embodiment examples shown in FIGS. 2E-F), stent 70 includes a series of crossovers 80 that differ from prior cross-overs and connectors previously described. Such difference is considered to provide certain particular benefits, especially when considered in combination with other beneficial features provided by the embodiment as elsewhere herein described. More specifically, cross-over 80 of stent 70 has a width 81 that is much larger than other cross-overs previously described, and including larger than that shown for the embodiment in FIGS. 1A-D. Prior designs provide cross-overs or connectors in a manner intended to provide certain degree of flexibility between adjacent segments along a stent. Such conventional cross-over regions most typically contribute a significant portion, and generally a majority, of the lateral flexibility of the overall stent during lateral flexure. However, according to the present embodiment, these cross-overs of substantial width represent very little, if any, of lateral flexure to the stent. This results from the substantial width given to the cross-overs relative to the remaining portions of the stent (eg. crowns, struts, and transition regions) all generally including smaller widths and thus less stiffness and more flexibility than the cross-overs. In particular, the tapering filament width along the extended transition region from struts to crowns within each stent segment, as noted above, flexibly absorb more flexure than experienced within the segments under other prior designs, and, as noted above, more than is experienced at the present stent's own cross-over.

The illustrative embodiment just described by reference to FIGS. 2A-D may be constructed of varied materials, and with varied particular dimensions, without departing from the broad aspects herein contemplated. However, for purpose of illustration, one particular construction exemplified by the physical embodiment shown in FIG. 2C-D is considered suitable, and of particular benefit, as follows. The stent intended to have 10 crowns/segment, 18 segments total, and about 1.0 mm segment length as illustrated for the current embodiment, is cut from cobalt-chromium alloy tubing. A cobalt-chromium tubing having "L605" alloy characteristics, 0.073 inch O.D./0.065 inch I.D. is used according to the present example. The laser cutting is conducted according to typical, suitable equipment and techniques, following two-dimensional CAD drawing provide, such as is shown in FIGS. 2A and 2C, and to achieve about the following dimensions by reference to those drawings (inches; post-cutting, but before post-processing such as electropolishing): overall length L=0.7170; transverse circumference T: 0.2300; crown overall width 89: 0.0110; crown-to-crown inter-segment spacing: 0.0030; segment amplitude (including spacing) 82: 0.0400; crown-to-crown period distance 88: 0.0230; maximum strut width (at constant width portion) 84: 0.0045; minimum width at transition region 100: 0.0031; length of constant straight edge section of strut 94: 0.0050; crown peak filament width 86: 0.0047; distance between centers of inner radius 83 and outer radius 85: 0.0015; inner radius 83: 0.0023; outer radius 85: 0.0055; radius 98: 0.0250; radius 99: 0.0150.

The specific geometries and dimensions for crossover 80 may vary and to suit a particular application or adaptation of other intercooperating elements in the stent 70. However, for the illustrative embodiment shown, the cross-over extends over a length generally representing the gap distance or spacing between adjacent facing crowns of adjacent segments, and is slightly radiused on each upper and lower edge. In this regard, further to the detailed description provided above for an exemplary physical embodiment, the crossover may have about the following dimensions (inches): outer radius of cross-over: 0.0055; cross-over width (at minimum dimension) 81: 0.0060.

After cutting a stent as just described, it is subsequently treated in standard fashion, including electropolishing, etc. to construct a particularly beneficial stent according to the present embodiment, with similar dimensions as noted above (generally slightly reduced from electropolishing and post-processing after laser cutting). A post-processing stent filament thickness in the radial plane of between about 0.0028 inches is believed to provide particular benefit in the overall design. Such a stent is then prepared for integration together with a delivery assembly (eg. crimping onto a balloon), packaging, sterilization, shipping, and for subsequent use.

According to the foregoing, it is clear that the present embodiment is considered to provide certain specific benefits arising from particular features shown and described. It is also to be made clear, however, that the current disclosure broadly contemplates substantial benefit afforded by certain broad aspects illustrated by the embodiments. These aspects are not necessarily to be limited by each specific feature provided in showing and describing the embodiments (though such may provide additional substantial benefit).

For example, one such broadly contemplated aspect provides a stent with serial expandable segments, interconnected with cross-overs or connectors, wherein the cross-overs or connectors contribute less lateral flexibility to the stent than is contributed within the segments themselves. According to one particular beneficial aspect of this, the most prominent lateral flexure is experienced along narrowed region of the struts, and a particular benefit is considered by providing this along a tapering region of transition between struts and crowns within a segment. These aspects and modes are considered unique to prior designs, as are further more detailed aspects such as providing the widest and/or stiffest portion of a strut-crown-crossover/connector design at the crossover/connector. In addition, other beneficial aspects of the present embodiment are found in the expansion characteristics that the tapering strut-crown transition provides in context of a crown design which has its greatest width at its peak, with tapering narrowing along its sides. While considered a valuable novel feature even if incorporated alone from this disclosure into prior designs, it is also considered to provide particular further benefit when combined with a strut-to-crown transition that has an extended, narrowing taper from a significantly abbreviated region of relatively constant width between crowns, toward a minimum width at the transition region adjacent to the crown. Staggering constant straight edge regions and radiused regions along opposite inner and outer edges relative to each other provides still further benefit.

It is to be further appreciated that various features, such as certain of those just described, may relate to each other, though may be also considered independently. For example, the embodiment of FIG. 2 provides a crown with increased width at its crown peak, inner and outer radii at the peak with offset relative centers, and increased strain distribution at the crown shoulders during radial expansion vs. at the crown peak. Each of these features relates to the other. For example, in the particular embodiment, the offset inner and outer radii provide one approach to result in a wider filament at the peak than at the shoulders. The wider filament at the peak is one approach to result in bifurcated strain distribution at the shoulders versus at the peak. Although these are interrelated as just described, they are not in all cases to be considered necessarily combined as such. For example, filament thickness in the radial plane, versus width in the circumferential plane, may be modified in order to bifurcate strain away from the crown peak and to the crown shoulders (even with constant width or even potentially more narrow width at the crown, depending on the extent of thickness variation). More specifically, by making the crown peak thicker than the shoulders, strain distribution may be shifted from the peak to the shoulders. In another example, inner and outer radii of the filament at the crown peak may be concentrically centered, yet the crown peak may still be wider than the crown shoulders. This may be accomplished for example by providing other combinations of radiused (or otherwise stepped or tapered) edges at the shoulders, such as for example vs. at the crown peak.

A closed-open-closed arrangement is provided by the embodiment just described, and is considered beneficial. More specifically, as elsewhere noted hereunder, the final two segments on each stent end include four crossovers between them, whereas the remaining intersegment positions along the stent between these ends contain two crossovers. While other aspects represented by the embodiment are considered broadly and accommodating of other crossover patterns or arrangements, this specific arrangement is considered of benefit, including without limitation in context of its combination with other features provided by this embodiment. In one regard, the four crossovers at each end provide sufficient stability at the ends to prevent linear collapse between the adjacent segments during use. The two crossovers between the other segments between the stent ends provide more flexibility that the four crossover region. Furthermore, the benefits of this crossover arrangement is considered to enhance performance in view of the use of the particular crossovers themselves of the embodiment, which are relatively wider and stiffer than other prior crossovers or interconnects (especially non-welded), and wider and stiffer than the more flexible locations along the intrasegment strut-crown transitions of this stent.

Notwithstanding the foregoing, however, it is to be appreciated that the particular combination of crown features provided by the current embodiment provide a particularly unique and valuable approach with distinct improvements presented over previously disclosed stents. Strain is distributed in a unique bifurcated manner to transitions at the crown shoulders and away from the crown peak. While strain of expansion and flexure are dictated by properties at these tapered transition regions at the crown shoulders, other areas with much lower strain contribution are widened. This enhances visibility without compromising performance by increasing radiopaque metal material to the low strain to no strain regions of the stent. This also provides areas of wider surface area to enhance local drug delivery. In contrast, other prior stents most typically provide uniform thickness along the filament, which is equal at focal strain regions and relatively low strain regions, versus engineering the undulating filament with customized features that vary along its length to maximize effectiveness of multiple variables. These multiple variables otherwise compete if given the same treatment at different regions. For example, to provide a strut thickness uniformly along the crown, it has certain constraints at the high strain region to provide certain expansion characteristics. Limiting the strut to the same constrained geometry at low strain regions compromises other performance features, such as for example radiopacity and surface area for enhanced local drug delivery.

In any case, these broad aspects contemplated within the present disclosure are to be considered of particular individual value, and without necessarily requiring their limitation by further more detailed features of embodiments herein specifically shown and described, though such more particular details are considered to present still further substantial benefit.

It is specifically contemplated that certain detailed aspects of the prior embodiments introduced above may be modified to suit a particular purpose, without departing from the broader aspects herein disclosed. For example, as shown in FIGS. 3A-6D, the particular number of crowns in a segment, or number of segments along a length of an overall stent, may be varied from those aspects shown for the specific embodiment in FIGS. 2A-2F above, but while preserving the various particularly beneficial features described for that specific embodiment.

In particular, FIGS. 3A-D illustrate a stent 110 that includes similar features with respect to crown, strut, transitioning region, and crossover design as noted for FIGS. 2A-F, but provides this combination of features in a "9 crown" per segment design versus the "10 crown" per segment design of the prior embodiment.

Figure 3A:
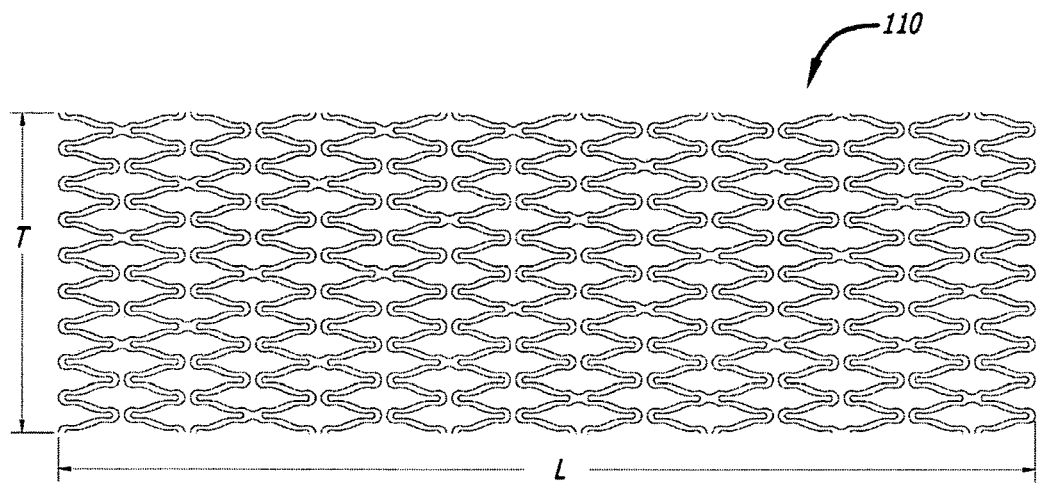
FIG. 3A shows a 2-D CAD drawing of another tubular stent of the present disclosure in longitudinally spliced and radially opened planar view.
Figure 3B:
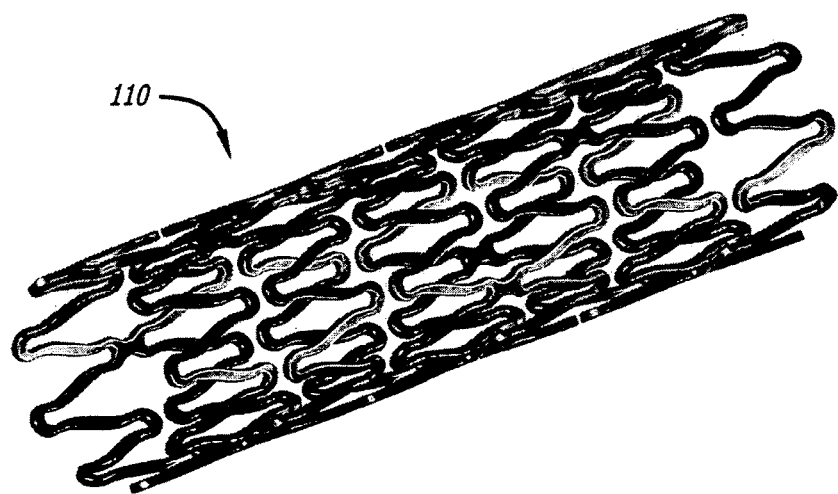
FIG. 3B shows a 3-D CAD illustration in angular perspective view of a stent of similar construction to that shown in FIG. 3A.
Figure 3C:
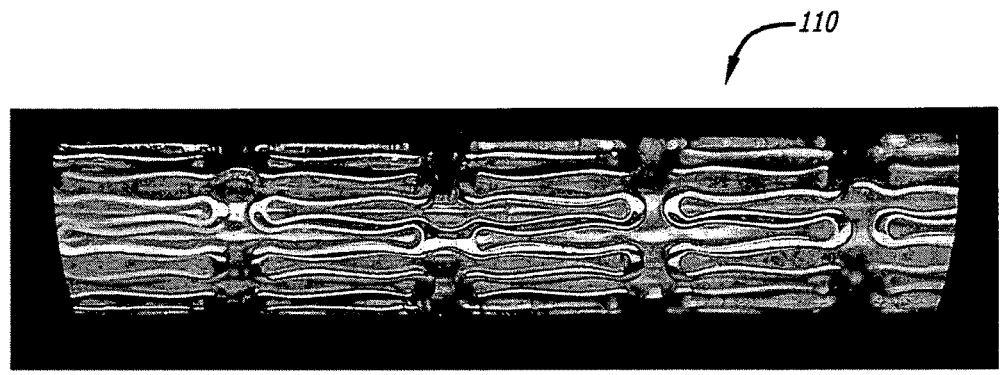
FIGS. 3C-D show photographs in side view at different respective magnifications of certain portions of a stent actually constructed to include similar features to the stent illustrated in FIGS. 3A-B.
Figure 3D:
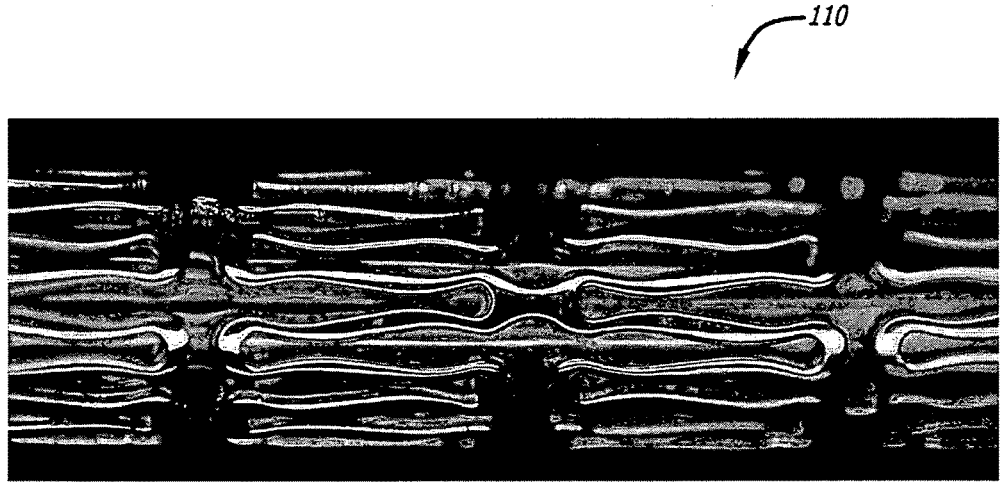

The illustrative embodiment just described by reference to FIGS. 3A-D may be constructed of varied materials, and with varied particular dimensions, without departing from the broad aspects herein contemplated. However, for purpose of illustration, one particular construction exemplified by the physical embodiment shown in FIG. 2C-D is considered suitable, and of particular benefit, as follows. The stent intended to have 9 crowns/segment, 18 segments total, and about 1.2 mm segment length as illustrated for the current embodiment, is cut from cobalt-chromium alloy tubing. A cobalt-chromium tubing having L605 alloy characteristics, 0.073 O.D./0.065 I.D. is used according to the present example. The laser cutting is conducted according to typical, suitable equipment and techniques, following two-dimensional CAD drawing provide, such as is shown in FIG. 3A, and to achieve about the following dimensions (inches; post-cutting, but before post-processing such as electropolishing): overall length L=0.7160; transverse circumference T: 0.2340; crown overall width: 0.0110; crown-to-crown inter-segment spacing: 0.0040; segment amplitude (including spacing): 0.0480; crown-to-crown period distance: 0.0260; maximum strut width (at constant width portion): 0.0045; minimum width at transition region: 0.0031; length of constant straight edge section of strut: 0.0075; crown peak filament width: 0.0047; distance between centers of crown inner radius and outer radius: 0.0015; inner radius: 0.0023; outer radius: 0.0055; larger strut transition region radius: 0.0250; smaller strut transition region radius: 0.0150.

The specific geometries and dimensions for the crossover per the current embodiment may vary and to suit a particular application or adaptation of other intercooperating elements in the stent 110 of the present embodiment. However, for the illustrative embodiment shown, the cross-over extends over a length generally representing the gap distance or spacing between adjacent facing crowns of adjacent segments, and is slightly radiused on each upper and lower edge. In this regard, further to the detailed description provided above for an exemplary physical embodiment, the crossover may have about the following dimensions (inches): outer radius of cross-over: 0.0065; cross-over width (at minimum dimension): 0.0057.

After cutting a stent as just described, it is subsequently treated in standard fashion, including electropolishing, etc. to construct a particularly beneficial stent according to the present embodiment, with similar dimensions as noted above (generally slightly reduced from electropolishing and post-processing after laser cutting). A post-processing stent filament thickness in the radial plane of about 0.0028 inches (eg. +/− about 0.0003 inches) is believed to provide particular benefit in the overall design. Such a stent is then prepared for integration together with a delivery assembly (eg. crimping onto a balloon), packaging, sterilization, shipping, and for subsequent use.

Figure 4:
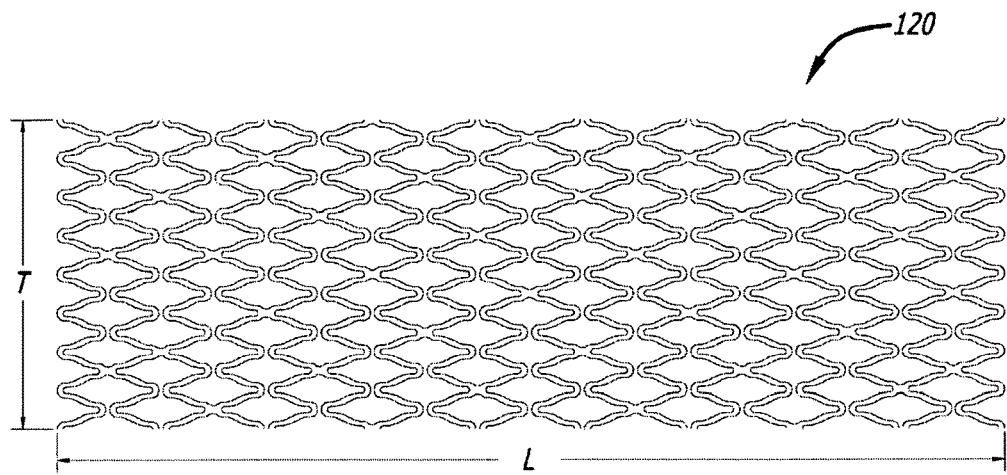
FIG. 4 shows a 2-D CAD drawing of another tubular stent of the present disclosure in longitudinally spliced and radially opened planar view.

FIG. 4 shows a stent 120 that represents an "8 crown" per segment embodiment, and which preserving the various beneficial featured shared between the 10 and 9-crown embodiments previously presented above with respect to FIGS. 2A-3D.

The illustrative embodiment just described by reference to FIG. 4 may be constructed of varied materials, and with varied particular dimensions, without departing from the broad aspects herein contemplated. However, for purpose of illustration, one particular construction considered particularly suitable for constructing a beneficially functional stent according to this embodiment is as follows. The stent intended to have 8 crowns/segment, 18 segments total, and about 1 mm segment length as illustrated for the current embodiment, is cut from cobalt-chromium alloy tubing. A cobalt-chromium tubing having L605 alloy characteristics, 0.073 O.D./0.065 I.D. is used according to the present example. The laser cutting is conducted according to typical, suitable equipment and techniques, following two-dimensional CAD drawing provide, such as is shown in FIG. 4, and to achieve about the following dimensions (inches; post-cutting, but before post-processing such as electropolishing): overall length L=0.7170; transverse circumference T: 0.2320; crown overall width: 0.0110; crown-to-crown inter-segment spacing: 0.0030; segment amplitude (including spacing): 0.0400; crown-to-crown period distance: 0.0290; maximum strut width (at constant width portion): 0.0045; minimum width at strut-crown transition region: 0.0031; length of constant straight edge section of strut: 0.0050; crown peak filament width: 0.0047; distance between centers of crown inner radius and outer radius: 0.0015; inner radius: 0.0023; outer radius: 0.0055; larger strut transition region radius: 0.0250; smaller strut transition region radius: 0.0150.

The specific geometries and dimensions for the crossover per the current embodiment may vary and to suit a particular application or adaptation of other intercooperating elements in the stent 120 of the present embodiment. However, for the illustrative embodiment shown, the cross-over extends over a length generally representing the gap distance or spacing between adjacent facing crowns of adjacent segments, and is slightly radiused on each upper and lower edge. In this regard, further to the detailed description provided above for an exemplary physical embodiment, the crossover may have about the following dimensions (inches): outer radius of cross-over: 0.0055; cross-over width (at minimum dimension): 0.0060.

After cutting a stent as just described, it is subsequently treated in standard fashion, including electropolishing, etc. to construct a particularly beneficial stent according to the present embodiment, with similar dimensions as noted above (generally slightly reduced from electropolishing and post-processing after laser cutting). A post-processing stent filament thickness in the radial plane of between about 0.0028 inches is believed to provide particular benefit in the overall design. Such a stent is then prepared for integration together with a delivery assembly (eg. crimping onto a balloon), packaging, sterilization, shipping, and for subsequent use.

Figure 5:
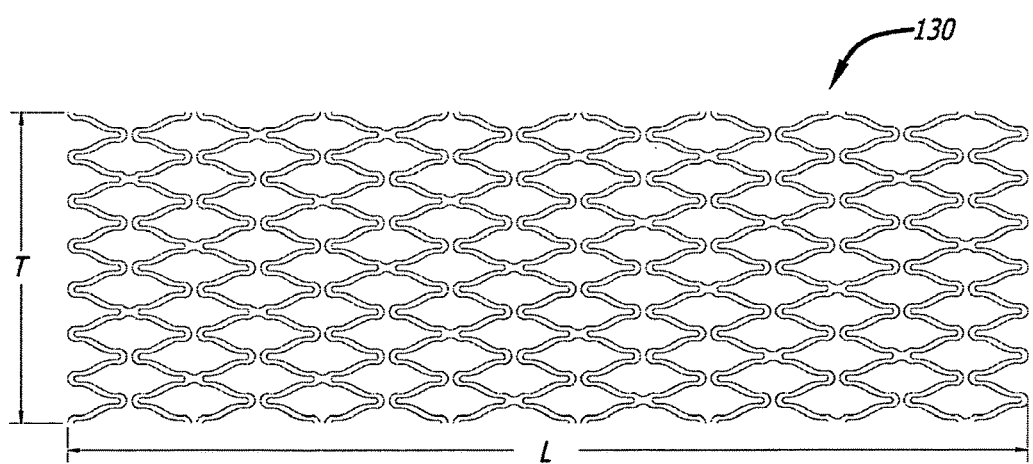
FIG. 5 shows a 2-D CAD drawing of another tubular stent of the present disclosure in longitudinally spliced and radially opened planar view.

FIG. 5 shows a stent 130 that represents a "7 crown" per segment embodiment, and which preserving the various beneficial features shared between the 10, 9, and 8-crown embodiments previously presented above with respect to FIGS. 2A-4.

The illustrative embodiment just described by reference to FIG. 5 may be constructed of varied materials, and with varied particular dimensions, without departing from the broad aspects herein contemplated. However, for purpose of illustration, one particular construction considered particularly suitable for constructing a beneficially functional physical stent of the present embodiment is as follows. The stent intended to have 7 crowns/segment, 15 segments total, and about 1.2 mm segment length as illustrated for the current embodiment, is cut from cobalt-chromium alloy tubing. A cobalt-chromium tubing having L605 alloy characteristics, 0.073 O.D./0.065 I.D. is used according to the present example. The laser cutting is conducted according to typical, suitable equipment and techniques, following two-dimensional CAD drawing provide, such as is shown in FIG. 5, and to achieve about the following dimensions (inches; post-cutting, but before post-processing such as electropolishing): overall length L=0.7160; transverse circumference T: 0.2310; crown overall width: 0.0110; crown-to-crown inter-segment spacing: 0.0040; segment amplitude (including spacing): 0.0480; crown-to-crown period distance: 0.0330; maximum strut width (at constant width portion): 0.0045; minimum width at strut-crown transition region: 0.0031; length of constant straight edge section of strut: 0.0075; crown peak filament width: 0.0047; distance between centers of crown inner radius and outer radius: 0.0015; inner radius: 0.0023; outer radius: 0.0055; larger strut transition region radius: 0.0250; smaller strut transition region radius: 0.0150.

The specific geometries and dimensions for the crossover per the current embodiment may vary and to suit a particular application or adaptation of other intercooperating elements in the stent 130 of the present embodiment. However, for the illustrative embodiment shown, the cross-over extends over a length generally representing the gap distance or spacing between adjacent facing crowns of adjacent segments, and is slightly radiused on each upper and lower edge. In this regard, further to the detailed description provided above for an exemplary physical embodiment, the crossover may have about the following dimensions (inches): outer radius of cross-over: 0.0065; cross-over width (at minimum dimension): 0.0057.

After cutting a stent as just described, it is subsequently treated in standard fashion, including electropolishing, etc. to construct a particularly beneficial stent according to the present embodiment, with similar dimensions as noted above (generally slightly reduced from electropolishing and post-processing after laser cutting). A post-processing stent filament thickness in the radial plane of between about 0.0025 inches to about 0.0031 inches, such as for example about 0.0028 inches, is believed to provide particular benefit in the overall design. Such a stent is then prepared for integration together with a delivery assembly (eg. crimping onto a balloon), packaging, sterilization, shipping, and for subsequent use.

Figure 6A:
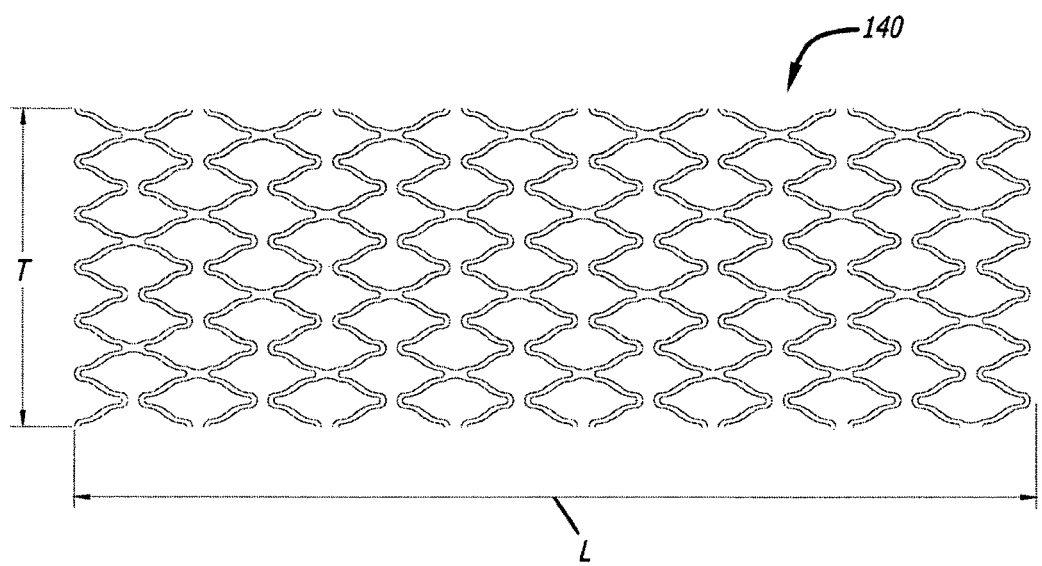
FIG. 6A shows a 2-D CAD drawing of another tubular stent of the present disclosure in longitudinally spliced and radially opened planar view.
Figure 6B:
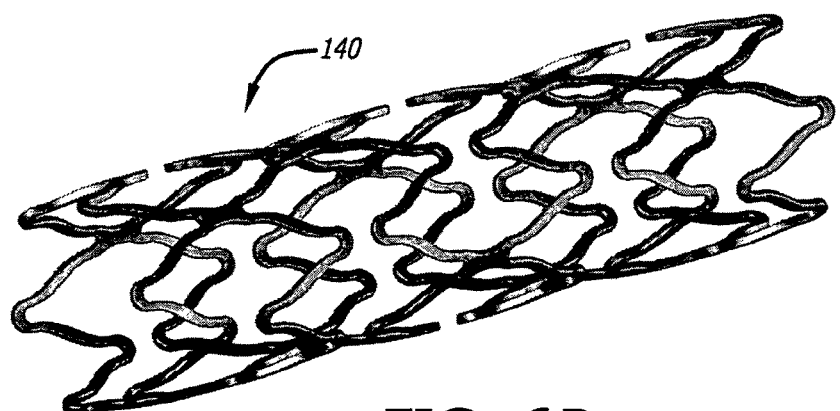
FIG. 6B shows a 3-D CAD illustration in angular perspective view of a stent of similar construction to that shown in FIG. 6A.
Figure 6C:
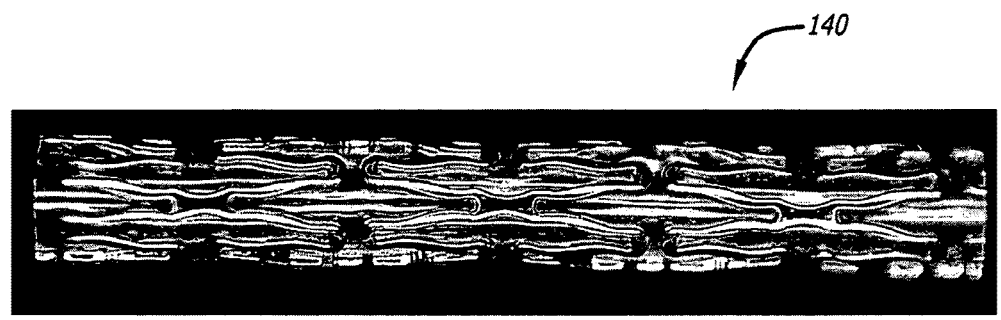
FIGS. 6C-D show photographs in side view at different respective magnifications of certain portions of a stent actually constructed to include similar features to the stent illustrated in FIGS. 6A-B.
Figure 6D:
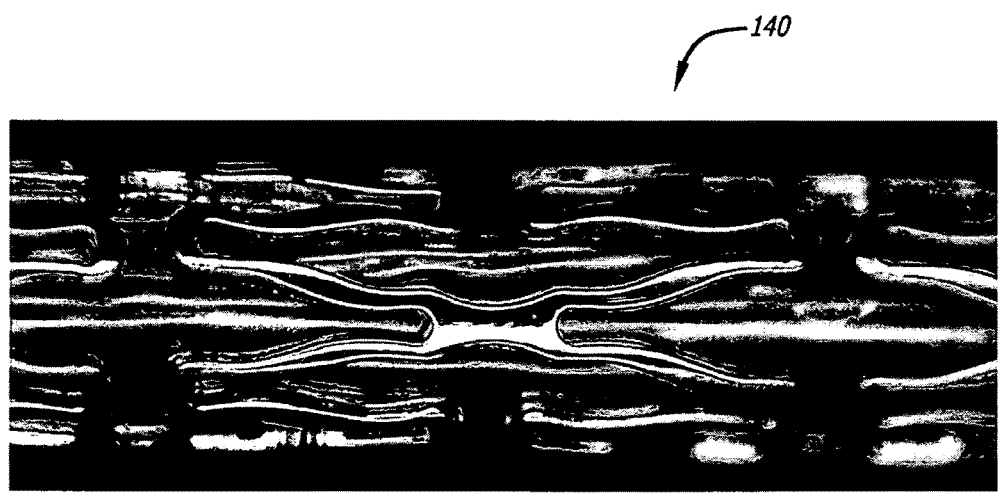

FIGS. 6A-D show a stent 140 representing a further "6 crown" embodiment, which also preserves the various beneficial features shared between the prior 10, 9, 8, and 7-crown embodiments represented in FIGS. 2A-5. Included for still further illustration are pictures of an exemplary physical embodiment constructed, as shown in FIGS. 6C-D.

The illustrative embodiment just described by reference to FIG. 6A may be constructed of varied materials, and with varied particular dimensions, without departing from the broad aspects herein contemplated. However, for purpose of illustration, one particular construction considered particularly suitable for constructing a beneficially functional physical stent of the present embodiment is as follows. The stent intended to have 6 crowns/segment, 15 segments total, and about 1.2 mm segment length as illustrated for the current embodiment, is cut from cobalt-chromium alloy tubing. A cobalt-chromium tubing having "L605" alloy characteristics, 0.073 O.D./0.065 I.D. is used according to the present example. The laser cutting is conducted according to typical, suitable equipment and techniques, following two-dimensional CAD drawing provide, such as is shown in FIG. 6A, and to achieve about the following dimensions (inches; post-cutting, but before post-processing such as electropolishing): overall length L=0.7160; transverse circumference T: 0.2340; crown overall width: 0.0110; crown-to-crown inter-segment spacing: 0.0085; segment amplitude (including spacing): 0.048 crown-to-crown period distance: 0.039; maximum strut width (at constant width portion): 0.042; minimum width at strut-crown transition region: 0.003; length of constant straight edge section of strut: 0.010; crown peak filament width: 0.042; distance between centers of crown inner radius and outer radius: 0.0012; inner radius: 0.0025; outer radius: 0.0055; larger strut transition region radius: 0.0250; smaller strut transition region radius: 0.0150.

The specific geometries and dimensions for the crossover per the current embodiment may vary and to suit a particular application or adaptation of other inter-cooperating elements in the stent 140 of the present embodiment. However, for the illustrative embodiment shown, the cross-over extends over a length generally representing the gap distance or spacing between adjacent facing crowns of adjacent segments, and is slightly radiused on each upper and lower edge. In this regard, further to the detailed description provided above for an exemplary physical embodiment, the crossover may have about the following dimensions (inches): outer radius of cross-over: 0.0150; cross-over width (at minimum dimension): 0.0060.

After cutting a stent as just described, it is subsequently treated in standard fashion, including electropolishing, etc. to construct a particularly beneficial stent according to the present embodiment, with similar dimensions as noted above (generally slightly reduced from electropolishing and post-processing after laser cutting). A post-processing stent filament thickness in the radial plane of between about 0.0022 inches and about 0.0035, such as between about 0.0025 inches and about 0.0031 inches, and more specifically about 0.0028 inches, is believed to provide particular benefit in the overall design. Such a stent is then prepared for integration together with a delivery assembly (eg. crimping onto a balloon), packaging, sterilization, shipping, and for subsequent use.

For a stent of a given number of segments, and similar overall length L and transverse circumference T, reducing the number of crowns in the manner illustrated by the various embodiments above will typically involve adjusting other geometric aspects of the design within a segment. This may include, for example, adjusting the strut angle between crowns, as fewer crowns around the circumference will generally translate to further crown-crown lateral distance between them for a given circumference. Moreover, this also generally corresponds with an increase in strut length to accommodate the increased spacing between crowns across which the struts traverse.

However, such variations between crown numbers is not necessarily intended to represent similar circumferences. For example, the embodiments of FIGS. 2A-4 representing similar stent designs in 8-10 crown per segment variations, respectively, may represent suitable alternative structures for intended expanded diameters between about 2.5 mm to about 4.5 mm, or in particular between about 3.0 mm to about 4.0 mm, such as for intended use in vessels requiring such sizing. Alternatively, similar stent designs, but that represent 6-8 crown per segment variations, may provide suitable structures for intended expanded diameters between about 2.0 to about 3.5 mm, or in particular between about 2.0 and 3.0 mm. Accordingly, where smaller vessels are intended for implantation, smaller expanded diameters are required of the stent implants and thus, for achieving a target range of coverage regarding stent filament material to vessel wall area, reduced crown numbers may be employed for the stent segments such as presently illustrated. In addition, varying crown numbers per segment may accommodate changing requirements where more open, or alternatively more closed, types of designs are desired for given applications but at a particular circumference.

Further to the foregoing, one particular exemplary kit of multiple stents (generally individually packaged separately for individual use) and amongst which to choose a device to accommodate alternative or variable sizing considerations. Illustrative examples of such kit and considered of particular benefit for use is as follows: 8 to 10 Crown stent for 3.5 to 4.5 mm vessel sizing; 5 to 8 crown stent for 2.5-3.5 mm vessel sizes; and 2-6 crown stent for <2.5 mm vessel sizes. A more specific example considered beneficial provides a 10 crown stent for 3.5 to 4.0 or 4.5 mm vessel sizing, and 8 crown stent for 2.5 mm to 3.0 or 3.5 mm vessel sizing. Appropriate labels are provided on each stent of the kit indicating its respective size range for intended use. However, it is to be appreciated that features such as crown numbers per segment, and related lumen wall coverage of the stent, may vary with respect to desired specifications for a particular application. Such variations of design over sizes, and related performance differences, will vary for example for different intended body environments to be stented, such as for example coronary vascular, neurovascular, renal, grafts, peripheral vascular, and other lumens such as in lungs, urinary tract, reproductive system, etc. The kits just described, and other embodiments and various features of the present disclosure, may vary between such different applications.

Accordingly, the various present aspects, modes, and embodiments are considered broadly and not necessarily limited to a specific kit of sizing and related design features for such sizes. For example, a range of 6 or more crowns could be used for larger vessels sizes of greater than 4.5 mm.

Another adjustment that may be made to accommodate reduction of crown numbers per segment, over a fixed length, may include reducing the number of overall segments. Moreover, other purposes may provide similar basis to adjust the number of segments over a length. When this is done, either or both of the length of the retained segments, and/or the spacing between them, is adjusted to achieve the overall length if such criteria is fixed (e.g. for a standard 18 mm stent length). The illustrative embodiments and examples shown in FIGS. 5-7B feature 15 segments along the respective stent lengths, versus 18 segments of the other embodiments of similar overall stent lengths such as shown in FIGS. 2A-4.

In addition to preserving the combination of beneficial features of FIGS. 2A-D while varying other features such as crown coverage in the stent segments, other features may also be varied. It is contemplated that while the particular combination of features shared among FIGS. 2A-6C provide significant and complimentary benefit, each such feature taken alone may provide benefit in certain circumstances without necessarily requiring the other.

Figure 7A:
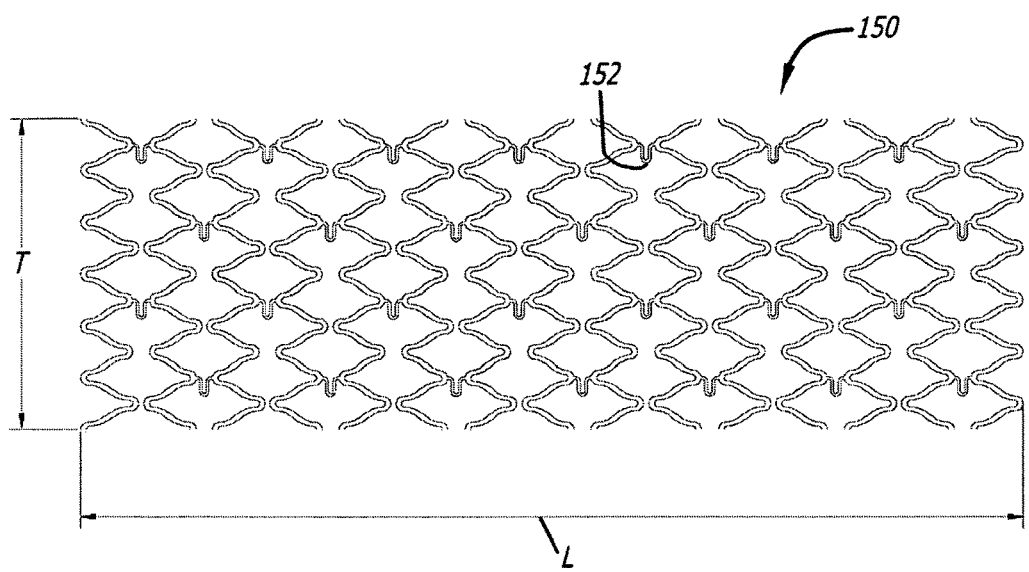
FIG. 7A shows a 2-D CAD drawing of another tubular stent of the present disclosure in longitudinally spliced and radially opened planar view.
Figure 7B:
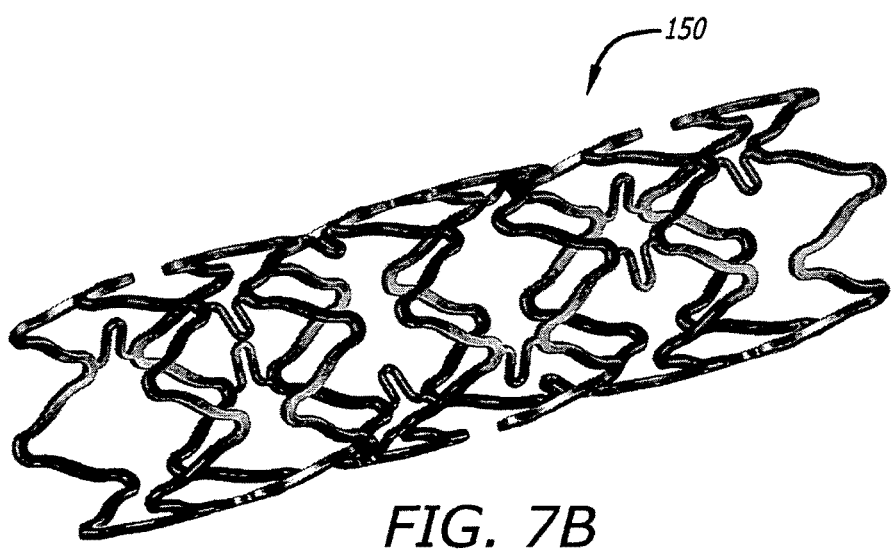
FIG. 7B shows a 3-D CAD illustration in angular perspective view of a stent of similar construction to that shown in FIG. 7A.
Figure 7C:
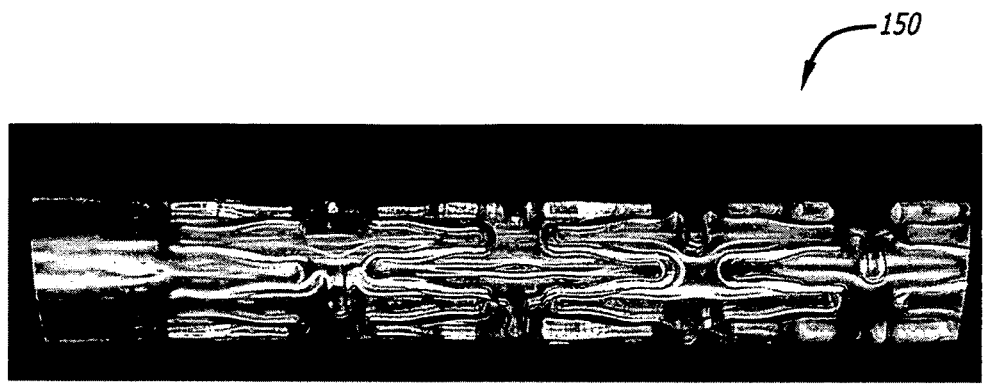
FIGS. 7C-D show photographs in side view at different respective magnifications of certain portions of a stent actually constructed to include similar features to the stent illustrated in FIGS. 7A-B.
Figure 7D:
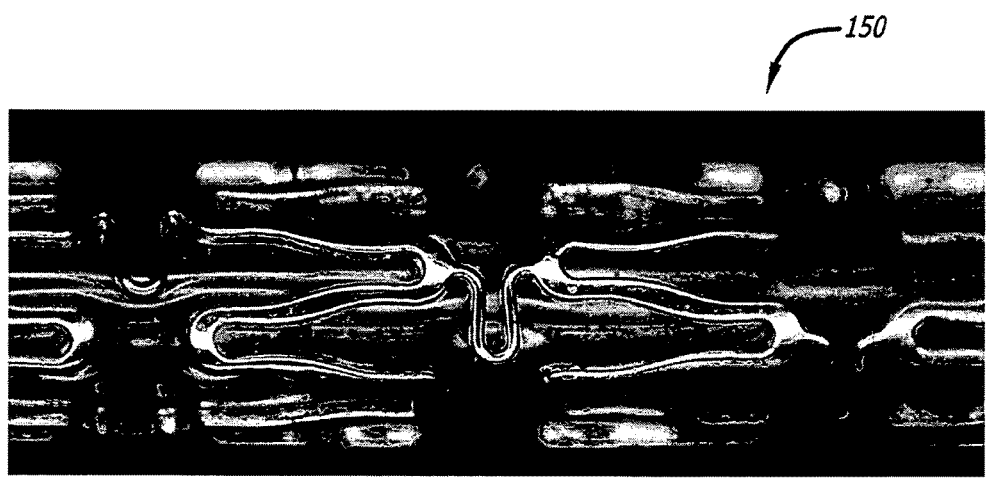
Figure 8A:
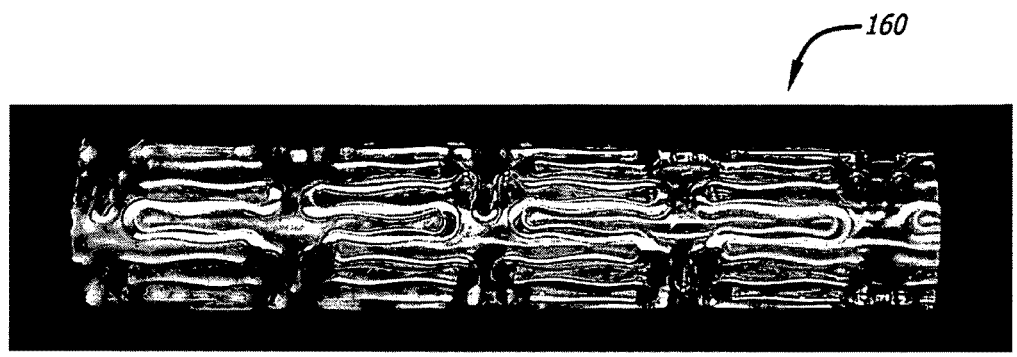
FIGS. 8A-B show photographs in side view at different respective magnifications of certain portions of another stent constructed according to certain further aspects of the present disclosure.
Figure 8B:
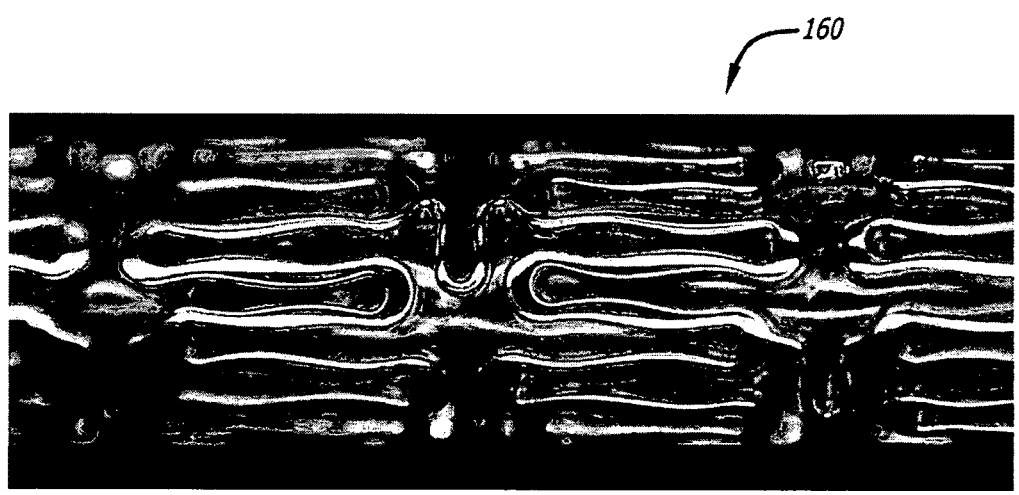

For example, as shown in FIGS. 7A-B, a stent 150 is provided in a "6 crown" per segment design as similarly shown for FIGS. 6A-C, and with similar beneficial features provided along the crowns and struts within the stent segments as shown for FIGS. 6A-C. However, in the present embodiment, an alternative cross-over 152 is shown that differs from that shown and shared among the prior embodiments of FIGS. 2A-6C (and differing still from the embodiment shown in FIGS. 1A-D). More specifically, crossovers 152 are of an intended "flexible" type, and include relatively thin "U"-shaped filament of substantially reduced width compared with the other filament portions of the stent (eg. crowns and struts). These "U"-shaped cross-overs are oriented in the transverse circumferential plane T lateral to the longitudinal axis L, allowing for the "U"-shape to flexibly expand longitudinally during lateral bending of the stent. This overall arrangement provides the particularly enhanced flexibility of the strut-crown transition region of prior embodiments above, with the additional flexibility provided at the crossovers. However, it is also apparent that the crown segments may be further spaced to accommodate these lateral "U"-shaped crossovers. This is readily seen by reference to stent 160 shown in FIGS. 8A-B as a physical embodiment example constructed to incorporate similar features to the embodiment shown in FIGS. 7A-B, but instead incorporating a "9-crown" per segment design.

The particular stent embodiments herein shown and described generally represent closed-open-closed approach to stent design, though incorporating various particularly beneficial aspects uniquely presented by the present disclosure. However, as elsewhere herein mentioned, certain aspects of the particular exemplary embodiments may be modified into forms other than those specifically shown, and particular beneficial features may be isolated from their combination with others in the present embodiments, without departing from the broad intended scope of various aspects herein contemplated. This includes with respect to the closed-open-closed arrangement of the stents described. The specific applications under this general arrangement shown in the embodiments may be altered to suit particular needs or desires. Or, the overall relationship of closed-open-closed within the stents may be modified to something different, and still incorporate other features presented by this disclosure as a distinct benefit.

One further stent herein contemplated provides an "open-closed-open" feature variation between the proximal, mid, and distal regions of the stent. This relationship between varied features along the stent length provides for greater flexibility characteristics at both ends of the stent. This feature can provide for a less abrupt transition between stented and unstented portions of a vessel and can also improve the deliverability of the stent.

Another stent of the present disclosure provides a "closed-open-closed" feature variation between the proximal, mid, and distal stent regions. This relationship is generally illustrated by the various present embodiments shown and described by reference to the Figures. In addition to the other benefits of such embodiments as elsewhere explained hereunder, this relationship between varied features along the stent length is also considered to be particularly beneficial for example when the area to be treated is in the vicinity of (i.e. found before and after) a vessel branch or bifurcation. The open middle portion of the stent provides for greater flexibility so that the stent can conform more readily to the irregular shape of this portion of the vessel. In addition, when treating a vessel in an area of a vessel branch or bifurcation, it is common for the stent to pass over the opening to the second vessel, thereby impeding blood flow into the second vessel (i.e. "gating" the vessel). A more open middle portion can reduce this "gating" effect and allow for better blood flow into the second vessel. Further, if needed, the nature of an open middle portion allows another stent to be deployed through the open middle portion into a gated vessel branch. Closed ends bordering the open middle portion provide better and more uniform support on each side of the vessel bifurcation.

Another stent herein contemplated provides a "closed-open" feature variation along the stent length. In one particular example, the stent is closed at its proximal end while becoming generally more open along the length of the stent. The "closed-open" embodiment can be advantageous when a more deliverable (i.e. more flexible distal end), yet supported stent is needed at a particular treatment site.

Still further, another stent herein contemplated provides an "open-closed" feature variation along its length, wherein the stent is open at its proximal end but is more closed distally along the length of the stent. This design is considered advantageous for example when the treatment site is relatively accessible (i.e. a more deliverable stent is not required). The closed distal end of this present stent provides uniform support while the open proximal end allows for a less abrupt transition between stented and unstented portions of the vessel. An open feature at the proximal end of the stent is considered especially advantageous because this is the area of a stented vessel that is more frequently observed to undergo restenosis using conventional devices. A treating physician may choose one of the various embodiments of the stents of the present invention depending on the particular site to be treated and the particular patient's treatment history.

As a guideline to determine whether a particular stent adopts a closed (proximal) to open (distal) arrangement, the stent can be divided into two equal portions (i.e. the same number of crossover, connector or weld point positions). If the number of crossovers, connectors or weld points is counted in each portion, the closed proximal portion should have at least one more crossover, connector or weld point than the open distal portion. Alternatively, to determine if a particular stent adopts a closed (proximal) to open (distal) design, the stent can be divided into two portions and a percentage of actual crossovers, connectors or weld points over possible spaces for crossovers, connectors or weld points can be calculated. With this calculation method, the open end of the stent would have a smaller percentage of crossovers, connectors or weld points than the closed end. While these methods can be done to make the determinations noted, they are not necessarily limiting so long as the spirit of the general descriptions and definitions are met, as would be apparent to one of ordinary skill.

These embodiments of the present disclosure have desirable characteristics when a particular treatment site requires a stent with enhanced deliverability characteristics. This embodiment might be chosen over an open-closed-open embodiment by a treating physician when the physician determines that the added support of a fully closed proximal end is desired at a particular treatment site.

As a guideline to determine whether a particular stent adopts an open (proximal) to closed (distal) embodiment of the present disclosure, the stent can be divided into two equal portions (i.e. the same number of crossover, connector or weld point positions). If the number of crossovers, connectors or weld points is counted in each portion, the open proximal portion should have at least one less crossover, connector or weld point than the closed distal portion. Alternatively, to determine if a particular stent adopts an open (proximal) to closed (distal) design, the stent can be divided into two portions and a percentage of actual crossovers, connectors or weld points over possible spaces for crossovers, connectors or weld points can be calculated. With this calculation method, the open end of the stent is required to have a smaller percentage of crossovers, connectors or weld points than the closed end.

These embodiments of the present disclosure have desirable characteristics when a particular treatment site is easily accessible. The closed portion of the stent provides required support while the open proximal end provides for a less abrupt transition from the stented to unstented proximal portion of the vessel. A less abrupt transition is especially advantageous at the proximal portion of the stented vessel because it is this area of the vessel that is otherwise most likely to suffer from restenosis.

The stents of the present disclosure can be used in any blood vessel, including, for example and without limitation, the coronary vasculature (which includes, without limitation, the right, left common, left anterior descending and circumflex arteries and their branches) and the peripheral vasculature (including, without limitation, branches of the carotid, aorta, femoral, renal, popliteal, and related arteries). While the stents of the present disclosure mainly have been described in terms of their use in a blood vessel, they can also be used in other lumens of the body, for example and without limitation, respiratory ducts, gastrointestinal ducts, bile ducts, the urinary system, the digestive tube, and the tubes of the reproductive system in both men and women.

The stents of the present disclosure can be coated with an appropriate material to enhance clinical performance. For instance, various coatings can be capable of releasing a drug or bioactive agent to assist in the repair of a diseased vessel and to assist in the prevention, treatment or inhibition of restenosis. Further, the stents of the present disclosure can be coated with a radiopaque material, such as a dye or marker to allow for better positioning during implantation. These coatings can be continuous or discontinuous on the surface of the stents and can be disposed on the interior and/or the exterior surface(s) of the stents. Coatings can include one or more layers and can be coated either directly onto the stents or onto a primer material on the stents.

A coating placed on the stents of the present disclosure should generally be biocompatible for most intended uses, in order to minimize adverse interaction with the walls of the vessel or duct lumen or with the liquid flowing through the lumen. However, some stent uses may be intended specifically to invoke a biological response, such as for example to promote vessel closure such as for aneurysm blockage etc. The coating may be of a durable type with sustained presence on the implant, or may be of a dissolvable or bioerodable type. The coating in many circumstances can consist of a polymeric coating material.

In one embodiment of the present disclosure the polymeric coating can have zwitterionic pendant groups, generally ammonium phosphate ester groups, for instance phosphoryl choline groups, or analogues thereof. Other examples of suitable polymers can be found in published International Patent Application Publication Nos. WO-A-93/16479 and WO-A-93/15775 which are hereby incorporated by reference for all they contain regarding polymers and coatings. Coatings used in accordance with the present disclosure also can consist of nonpolymeric coating materials. The coating also can include a metallic coating placed onto the surface of the stent through electro- or electroless deposition processes. These may be to provide a desired surface characteristic, or may be loaded with a radiopaque or bioactive agent that elutes from the coating or otherwise interacts with the implant's environment in a desired way.

Many substances that can enhance clinical performance can be included in coatings of the stents of the present disclosure. For instance, a radiopaque material, such as a dye or marker can be used to allow for better positioning during implantation. These markers can be placed on the ends of the stents as well as to mark the location of an open or closed portion of the stent. Drugs and bioactive agents that can enhance the clinical performance of the stents of the present disclosure also can be included. Examples of such drugs and bioactive agents include, for example and without limitation, antineoplastic, antinflammatory, antiplatelet, anticoagulant, antifibrin, antithromobin, antimitotic, antibiotic, antiproliferative and antioxidant substances, as well as calcium channel blockers, colchicine fibroblast growth factor antagonists, histamine antagonists, 3-hydroxy-3-methylglutaryl coenzyme A (HMG-CoA) reductase inhibitors, monoclonal antibodies, phosphodiesterase inhibitors, prostaglandin inhibitors, platelet-derived growth factor antagonists, serotonin inhibitors, steroids, and thioprotease inhibitors. Additional substances can include, for example and without limitation, rapamycin, cladribine, heparin, nitrous oxide, nitric oxide, actinomycin D, as well as, alpha-interferon, genetically engineered epithelial cells, and fish oil (omega 3-fatty acid), des-aspartate angiotensin I, angiotensin converting enzyme (ACE) inhibitors, angiotensin receptor blockers (ARBs), statins (including without limitation cerivastatin), hormones, and estradiol. Various combinations of such bioactive agents and compounds, and analogs or derivatives of them, are further contemplated and not to be considered a departure from the intended scope of this disclosure.

In addition to other references herein incorporated by reference, the following issued U.S. Patents are also herein incorporated in their entirety by reference thereto: U.S. Pat. Nos. 6,293,967; 6,527,799; 6,540,774; 6,652,579; 6,796,997; and 7,018,400. The following published U.S. patent applications are also herein incorporated in their entirety by reference thereto: US 2005/0119723; 2006/0050011; 2006/0100695; and 2006/0115512. The following PCT Patent Application Publications are also herein incorporated in their entirety by reference thereto: WO 2004/028571; WO 2005/053766; WO 2007/024484.

It is to be understood that the present invention is not limited to the particular embodiments, materials, and examples described herein, as these can vary, though such particularities provided in the disclosure are considered nonetheless of particular further value and benefit to the broader aspects and modes also contemplated. It also is to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "a stent" is a reference to one or more stents and includes equivalents thereof known to those skilled in the art and so forth.

Unless defined otherwise, all technical terms used herein have the same meanings as commonly understood by one of ordinary skill in the art to which this invention belongs. Specific methods, devices, and materials are described, although any methods and materials similar or equivalent to those described herein can be used in the practice or testing of the present invention.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law.

Moreover, any combination of the above-described elements in all possible variations thereof is encompassed by the invention unless otherwise indicated herein or otherwise clearly contradicted by context.

Furthermore, numerous references are herein made to patents and printed publications throughout this specification. Each of the above cited references and printed publications are herein individually incorporated by reference in their entirety.

It is to be understood that the particular embodiments disclosed herein are illustrative of various broad aspects and modes of the present invention. Each aspect, mode, embodiment, and feature is considered of independent value and benefit without requiring limitation by their combinations or further refinements described, though such combinations and refinements are considered of still further benefit and value. Other modifications that may be employed by one of ordinary skill are considered within the scope of the invention though such may not specifically described hereunder. Thus, by way of example, but not of limitation, alternative configurations of the present invention may be utilized in accordance with the teachings herein. Accordingly, the present invention is not limited to that precisely as shown and described.

Example #1

I. Introduction

Certain aspects of exemplary stent constructions consistent with the present embodiments were modeled using 3-Dimensional Finite Element Analysis (3-D FEA). These 3-D FEA models were subjected to certain simulated deflection forces in order to calculate, represent, and evaluate material strain distributions variously within and between representative stent segments of the models under conditions related to radial expansion and lateral bending, respectively.

Similar 3-D FEA modeling and simulation was performed for two additional stent designs intended to represent certain commercially available stents. More specifically, these two additional stent models were intended to represent certain aspects of two cobalt-chromium stents of different designs, and from two different manufacturers, and that represent the top selling bare metal stents in the world: the "DRIVER®" stent commercially sold by Medtronic, and the "VISION®" stent commercially sold formerly by Guidant (currently sold by Abbott Vascular).

The 3-D FEA strain distributions during simulated radial expansion and lateral bending, respectively, were displayed with varied shading along the 3-D models, with results compared between the various stents modeled.

II. Materials and Methods

The LS-DYNA finite element program (Version 971) was used to analyze stress-strain simulations of computer generated samples for exemplary stent segments during (a) balloon expansion and (b) local bending at the crossovers.

3-D FEA models were created that were intended to represent: (i) a "Model #1" for a stent constructed to incorporate similar strut, crown, and cross-over features as that described above by reference to FIGS. 1A-D, according, however to an 8-crown per segment design; (ii) a "Model #2" intended to represent a stent constructed with strut-crown segment features constructed according to various aspects in common with those as described for the exemplary embodiment above for FIGS. 2A-D, according, however to a 10-crown per segment design (iii) a "Model #3" intended to represent a stent constructed to incorporate strut-crown segment features similar to the embodiment of FIGS. 1A-D, but incorporating crossover features similar to that of each of the embodiments of FIGS. 1A-D and FIGS. 2A-D (for comparison purposes in lateral bending simulation), and as also presented in an 8-crown per segment design; (iv) a "Model #4" intended to illustrate certain aspects similar to a Driver® stent, and (v) a "Model #5" intended to illustrate certain aspects similar to a Vision® stent.

Drawings for Models #1 and #2 were based upon 2-D CAD drawings used to manufacture the stents, such as provided in FIGS. 1A and 2A, respectively, for the features simulated, and per exemplary dimensions provided for various aspects noted above (adjusted for generally expected outcomes post-processing to finished goods, such as electropolishing). Similar 2-D CAD drawings were used to create Model #3. 2-D CAD drawings for (iii) Driver® and (iv) Vision® were created, and the 3-D modeling completed, based upon inputs that reflected dimensional measurements taken from commercially available products, respectively.

Material properties of a cobalt-chrome alloy (L605) were used for all models in order to isolate variables to highlight affects of design differences on the performance features evaluated. An elastic modulus of 243 GPa, yield stress of 547 MPa, and a plastic modulus of 24 GPa were used as material parameters for the analyses. It is understood that the Vision® incorporates such similar L605 alloy in the commercial stent sold, whereas the Driver® incorporates a different cobalt-chrome alloy called "MP35N." However, in order to understand comparative impact between design features of the various models in the study, L605 properties were applied to all modeled stents in the study. It is noted however to make clear, the estimated dimensions and specific material properties assigned to the modeled stents based upon these commercial stents likely do not match those actual stents with perfect accuracy. Thus, this study, and results and conclusions made, relate only to "estimated models" considered to have certain "similarities" with these commercial stents, but do not directly represent those actual commercial stents or their manufacturers, nor capture or represent their actual characteristics or performance.

Radial expansion of the stent was simulated as follows. Initial stent crimping from the "cut" sizes to reduced "delivery" sizes was simulated using non-compliant cylindrical mandrels. The modeled stents in the simulated crimped conditions were then subjected to the simulated radial expansion and lateral bending. The radial expansion simulation was conducted to a maximum diameter under assumed parameters representing a balloon inflated to 16 atm. These simulated steps were performed to ensure the proper work hardening and strain history for an elastic-plastic response. This simulated radial expansion was performed for each of Models #1-2 and #4-5.

Local bending was simulated by placing a radial displacement at the crossover connection and allowing the region between and including adjacent crowns of the stent to react to the compressive load. While not specifically a direct simulation of lateral bending of a completed tubular stent constructed according to the models, this set-up is believed to provide an indication of strain distribution within and between the modeled stent segments during bending, such as for example whether (and to what extent) the crossover would allow a focal bend using the radial force produced by the stent. The lateral bending simulation was performed for all Models #1-5.

Results were displayed in 3-D FEA renderings of the various stent features analyzed. Colorimetry and shading was performed to display strain distribution, according to a color palette that varies from low to high strain. Black and white or grey-scale representations of the strain distribution were also captured for the 3-D FEA models, and variously formed the bases for the respective visual renderings provided in the respective Figures referenced hereunder. More specifically, in these FIGS. 9-17, lighter shading generally represents lower strain, with darker shading representing higher strains.

III. Results

A. Radial Expansion Simulation
1. Model #1

Figure 9:
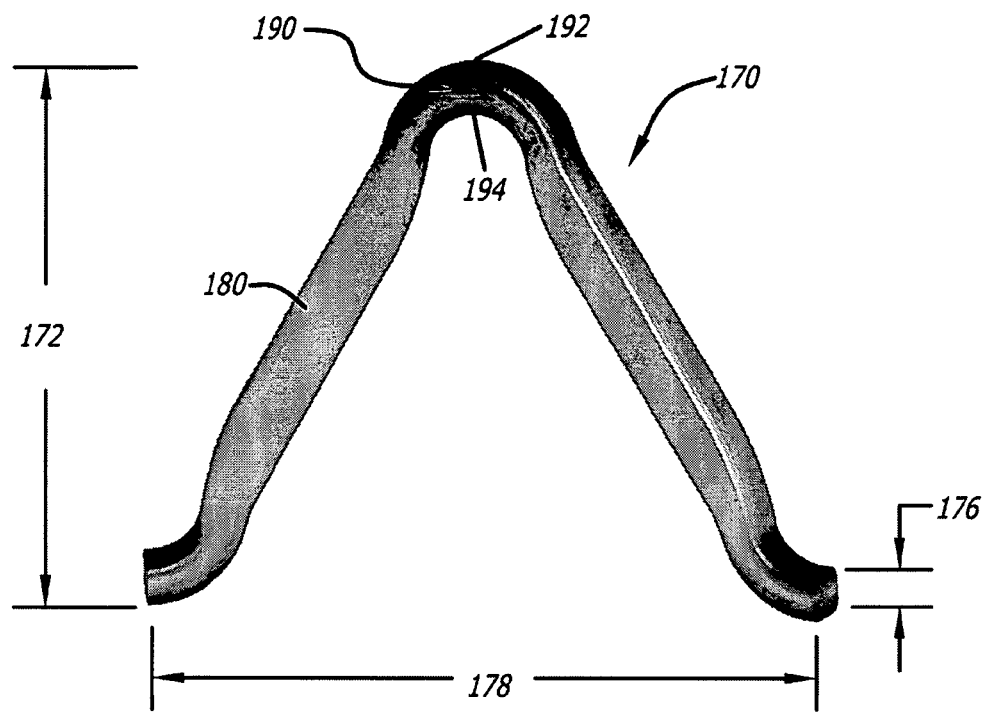
FIG. 9 shows a computer simulation of a representative portion of a stent modeled according to one particular construction sharing certain similar features with the stent embodiment illustrated in FIGS. 1A-D, and as subjected to radial expansion simulation under computer finite element analysis (FEA), and shows shading to reflect varied levels of material strain along the modeled structure in the simulation.

FIG. 9 shows a 3-D FEA simulation and reflecting strain distribution during simulated radial expansion for a peak-peak full period section of Model #1. More specifically, FIG. 9 shows a stent 170 having a peak-peak amplitude 172 and constructed as to its section features (eg. strut, crown, and transition therebetween) similar to that embodiment described above by reference to FIGS. 1A-D, provided here in an 8-crown per segment design. Strain distribution is shown with respect to struts 180, crown 190 (including its outer and inner radii 192, 194), and as revealed through the cross-sectioned reduced thickness region 176 located at the crown peak in this particular embodiment. Dark shading representing higher levels of material strain is isolated to only outer and inner radii 192, 194 of the crowns 190. The significant extent of the struts 180 are shown to reflect very low relative strain. Accordingly, it is evident that material strain of Model #1 during radial expansion is principally concentrated (and thus most of its expansion deformation occurs) along the sweeping outer and inner radii 192, 194 of its crowns 190.

2. Model #2

Figure 10:
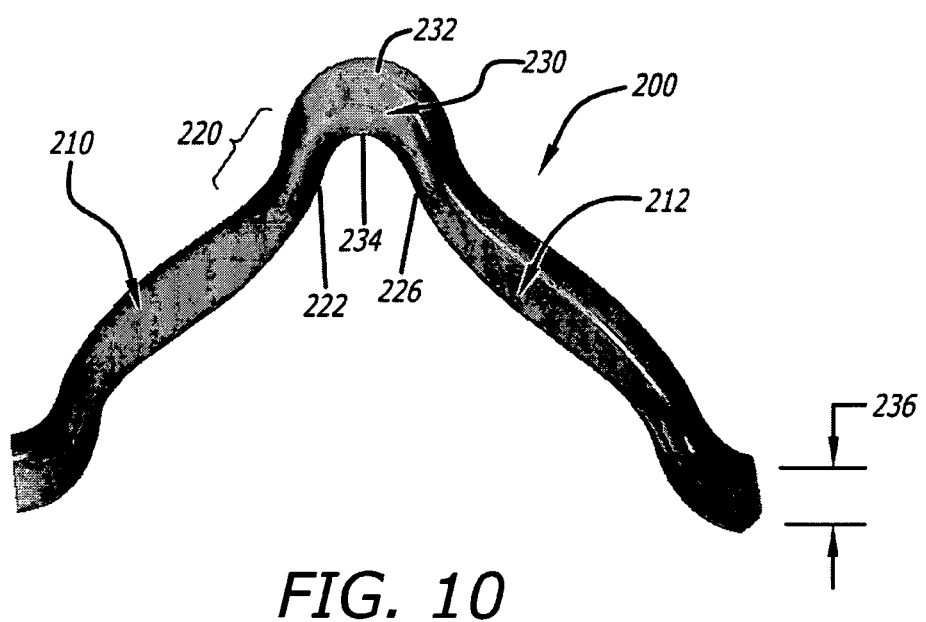
FIG. 10 shows a computer simulation of a representative portion of another stent modeled according to one particular construction sharing certain similar features with the stent embodiment illustrated in FIGS. 2A-F, and as subjected to radial expansion simulation under computer FEA, and shows shading to reflect varied levels of material strain along the modeled structure in the simulation.

FIG. 10 shows a 3-D FEA simulation and reflecting strain distribution during simulated radial expansion for a peak-peak full period section of Model #2. More specifically, FIG. 10 shows a stent 200 modeled as to its sectional features (eg. strut, crown, and transition region therebetween) similar to that embodiment described above by reference to FIGS. 2A-D, provided here in an 10-crown per segment design. Strain distribution under simulated radial expansion environment is shown with respect to the struts 210, crowns 230 (including the outer and inner crown radii 232, 234), transition shoulder region 220 between strut 210 and crown 230, and as revealed through the cross-sectioned reduced thickness region 236 located at the crown peak in this particular embodiment. The strain experienced under expansion, while more concentrated than the stress distribution for the sample, appears to be distributed in a unique manner. Of particular note, the crown 230 appears to be devoid of, or at least experience very little, strain at its peak (eg. at its midline, such as centrally between struts 210 and 212), including centrally in the strut and at the outer radius 232 and inner radius 234 in this area. In fact, this central crown region appears to experience the least strain of all regions represented along the full period of crown-strut-crown-strut-crown represented. This exceptionally low stress, light shading is further reflected through the partial cross-section taken through the crown peak midline at 236. Rather than strain distribution across the crown and concentrated most at this peak, as observed with other designs (such as Model #1), the expansion strain appears to be distributed in a bifurcated manner to the opposite transition shoulder regions 220 at either of sides 222, 226 where crown 230 transitions into each of the two adjacent struts 210, 212 extending therefrom.

Accordingly, it is clear that the crown peak regions, as the maximum width regions among the crown and strut (and transition region) features of this design, are demonstrably the lowest expansion strain region of the stent (including lower than the mid-strut regions). Highest strain is reflected at tapering transition regions 220 between strut 210 and crown 230, with the strain concentration bifurcated to either side of each crown.

3. Model #4

Figure 11:
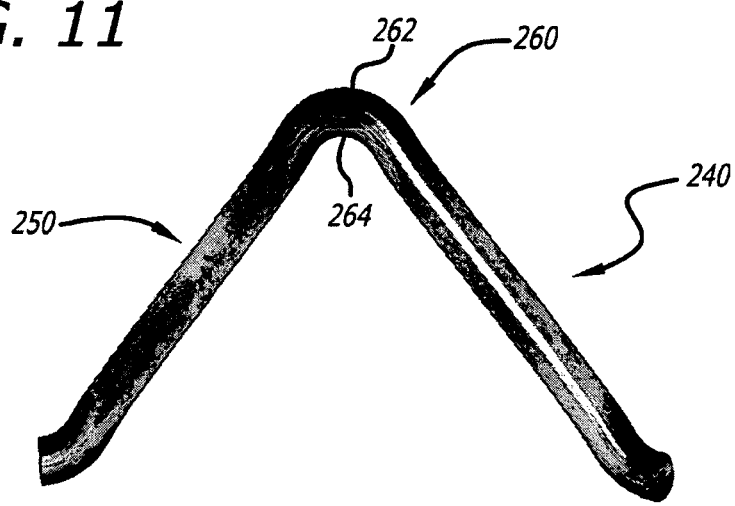
FIG. 11 shows a computer simulation of a representative portion of another stent modeled according to another particular construction intended to represent certain features and characteristics of a first commercially available stent, and as subjected to radial expansion simulation under computer FEA, and shows shading to reflect varied levels of material strain along the modeled structure in the simulation.

FIG. 11 shows a 3-D FEA simulation and reflecting strain distribution during simulated radial expansion for a peak-peak full period section of Model #4. More specifically, the simulated stent 240 includes a generally uniform filament thickness along the entire strut-crown section, and simply features abrupt bends as "elbows" in an otherwise generally uniform filament of fairly constant thickness. This simple bent elbow crown feature bent into an otherwise generally constant thickness filamental structure of this model contrasts against other stents with designed "crowns" with otherwise unique geometric features, such as provided in various forms throughout the present embodiments. For example, in comparison, the crown region of Model #1, while a more simple arcuate design than for Model #2, nonetheless features a reduced filament thickness versus the corresponding struts in a manner different than this Model #4.

As seen in FIG. 11, the strain distribution under simulated radial expansion for Model #4 appears generally isolated to the outer and inner radii 262, 264 its elbows 260. The entire length of the strut 250 bridging between opposite facing elbows 260 reveals very little strain along these features.

4. Model #5

Figure 12:
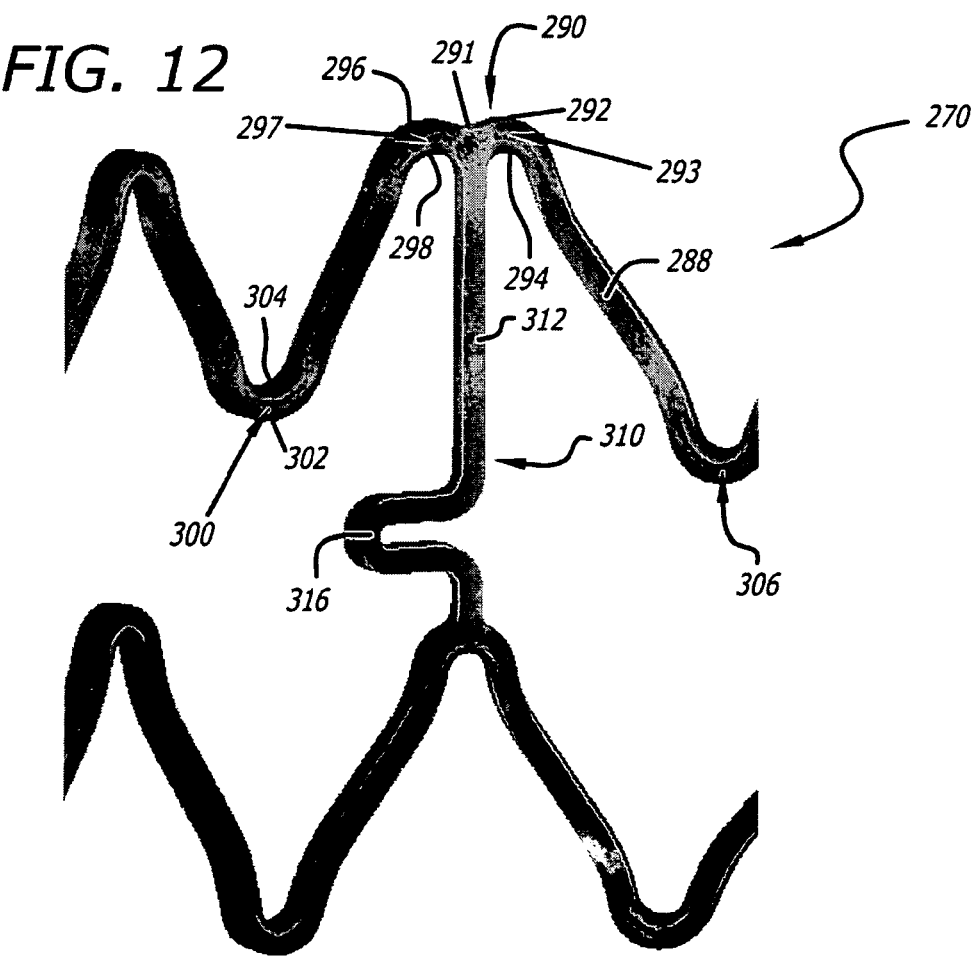
FIG. 12 shows a computer simulation of a representative portion of another stent modeled according to another particular construction intended to represent certain features and characteristics of a second commercially available stent, and as subjected to radial expansion simulation under computer FEA, and shows shading to reflect varied levels of material strain along the modeled structure in the simulation.

FIG. 12 shows a 3-D FEA simulation and reflecting strain distribution during simulated radial expansion for a peak-peak full period section of Model #5. More specifically, the modeled and simulated stent 270 includes undulating filament pattern with varied types of crowns and a crown-valley arrangement connecting adjacent segments (ie. a connector bridges between a crown peak of one segment facing one direction and a valley of a crown of an adjacent segment facing the same direction). More specifically, the stent 270 includes a connector 310 with a straight portion 312 and a "U"-shaped portion 316. Straight portion 312 connects to crown 290 fairly centrally of the crown 290, whereas the "U"-shaped portion 316 of the connector 310 is located between segments and oriented transverse to the long axis of portion 312 and central axis of crown 290. Crown 290 includes a subtle notch or valley 291, rather than a peak, at its midline where connector 310 is connected. Notch 291 sits between two partial peaks or bulbs 293, 297 on either side of the connector 310. These two adjacent bulbs 293, 297 include right and left outer and inner radii 292, 294 and 296, 298, respectively. Struts 286, 288 connect either side of crown 290 to adjacent, opposite facing crowns 300 and 306. The amplitude between crown 290 and crown 300 is shorter than that between crown 290 and crown 300, in order to provide additional space with the adjacent segment in which laterally oriented "U"-shaped member 316 of connector 310 may reside.

According to these basic features for the Model #4 just described, FIG. 12 shows the strain distribution is virtually entirely focused within the respective outer and inner radii of each of crowns 290, 300, and 306. This is shown for example at outer and inner radii 302, 304 for crown 300, as well as at outer and inner radii for the other crowns (eg. at 296, 298 and 292, 294). Outside of these focal regions, the simulation reveals little to no material strain or deformation in other regions during expansion, such as for example struts 288 or connector 310.

B. Lateral Bending Simulation

1. Model #1

FIG. 13 shows a 3-D FEA simulation and reflecting strain distribution during simulated lateral bending deflection for a two adjacent segment portion of stent 170 of Model #1 as follows. As is apparent under the simulated force of deflection, strain appears to be significantly localized to crossovers 184, and in particular at their outer and inner surfaces 184, 188 (with respect to the central axis within the simulated tube around which the stent surrounds). Very little strain or material deformation appears to be experienced at other regions other than the cross-overs under the environment of this simulation, including for example along struts 180 or at crowns 190, including at their outer and inner radii 192, 194.

2. Model #2

FIG. 14 shows a 3-D FEA simulation and reflecting strain distribution during simulated lateral bending deflection for a two adjacent segment portion of stent 200 of Model #2 as follows. Cross-overs 238 between segments appear to experience very little strain, and certainly do not appear to be a site of local strain concentration, despite force of bending being applied at their location. Rather, strain appears to be located principally at the transition regions 220 between the respective crowns 230 and struts 210, 212 in the design. Whereas a disparity in strain concentration appears in FIG. 14 between each adjacent transition region 220 on either side of the crown 230 associated with a cross-over being deflected, this (and other artifacts such as other bending responses to the simulated applied deflection forces) is believed to represent an artifact of certain boundary parameters and respective constraints of the simulated environment. It is believed that the region of strain concentration at the transition regions 220 would be fairly uniformly distributed to either side of a given crown in a full stent of similar construction as the portion shown for Model #2, and under applied forces such as intended to be simulated here.

3. Model #3

Figure 15:
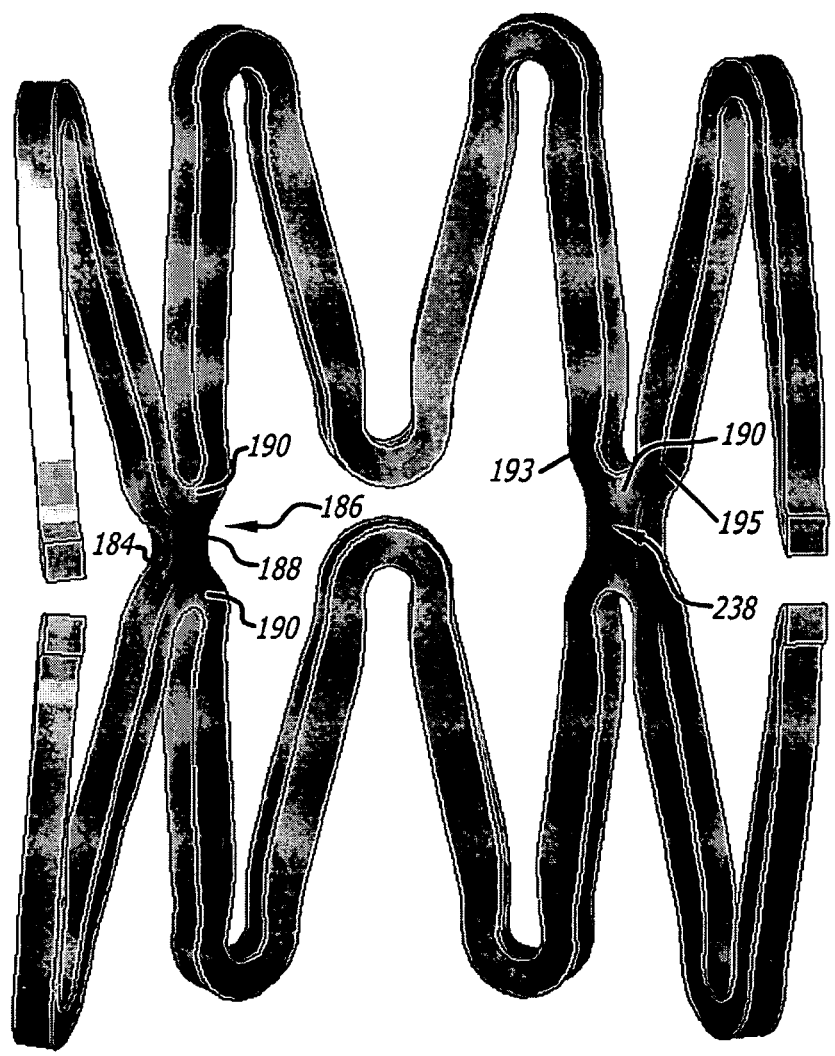
FIG. 15 shows a computer simulation of another representative portion of two adjacent segments of another stent modeled to include certain features similar to those of each of the stents modeled in FIGS. 9-10 and 13-14, and similar to the embodiments illustrated in FIGS. 1A-D and FIGS. 2A-F, as subjected to a different lateral bending simulation under computer FEA, and shows shading to reflect varied levels of material strain along the modeled structure in the simulation.

FIG. 15 shows a 3-D FEA simulation and reflecting strain distribution during simulated lateral bending deflection for a two adjacent segment portion of Model #3 as follows.

The stent 170 shown for Model #3 in FIG. 15 is constructed with "segment" features (e.g. struts 180, crowns 190, crown outer and inner radii 192, 194) similar to Model #1. Stent 170 of Model #3 also includes crossover 186 similar to Model #1. However, Model #3 differs from Model #1 by also providing another cross-over more similar to those provided in Model #2. A further embodiment of the present disclosure is thus presented, which combines the segment features similar to Model #1 with a cross-over feature similar to Model #2, and is explored as to certain characteristics during simulated lateral bending. In doing so, for a stent of one similar design as to its "segment" features (eg. Model #3 is similar to Model #1), the affects of different cross-overs between segments may be evaluated during lateral bending simulation. In addition, this "hybrid" aspect of Model #3 also provides an ability to compare lateral bending strain distributions between stents sharing a similar cross-over feature between adjacent segments, but with different segment features, eg. the different strut, crown, and strut-crown transition segment features of Model #3 (similar to Model #1) and Model #2.

As shown in FIG. 15, strain distribution at cross-over 186 appears to be very similar to that for Model #1 during lateral bending. This result is sensible as virtually all local features, crowns, struts, transitions, and cross-over, are similar between the models in this region of Model #3. However, the strain associated with lateral deflection forces at the region around the other cross-over 238 appears to be uniquely distributed versus the other Model #1 above. Here, strain appears to be distributed across a region that principally includes most strain spread across the adjacent lateral shoulders 193, 195 on either side of the peaks for the opposite facing crowns 190 on either longitudinal side of cross-over 238. However, a slight strain appears to bridge between the opposite facing crowns across the inner surface of cross-over 238. This relatively widely spread strain distribution in this region, with highest levels at the two pairs of opposite crown shoulders involved, is believed to result from the geometry of in the design with the shoulders representing the smallest width region of the overall design, and largest width region being the cross-over. While this cross-over is larger in width, and of equal thickness, than the struts, the slight strain distribution seen there on its inner surface is believed to be mostly isolated to a propagated result, featured mostly at the unbound surface, responding to the focal strain in the four adjacent regions.

4. Model #4

Figure 16:
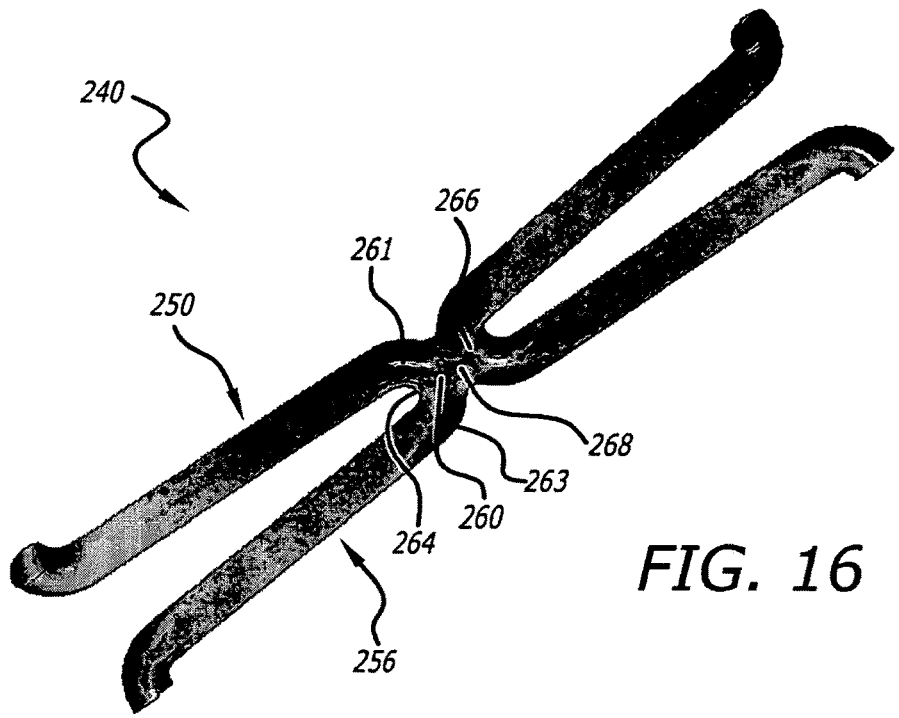
FIG. 16 shows a computer simulation of another representative portion of two adjacent segments of a similar stent model as that shown in FIG. 11 and intended to represent certain aspects of a first commercially available stent, although as subjected to a different lateral bending simulation under computer FEA, and shows shading to reflect varied levels of material strain along the modeled structure in the simulation.

FIG. 16 shows a 3-D FEA simulation and reflecting strain distribution during simulated lateral bending deflection for a two adjacent segment portion of Model #4 as follows.

According to the representation of Model #4 shown, stent 240 includes two adjacent opposite facing elbows 260, 266 that are welded together, and their weld joint therebetween forms the connection or linkage 268. Strain appears to be concentrated principally at the shoulder regions 261, 263 of these connected elbows 260, 266 on either side of their weld connection 268. The struts 250, 256 bordering either side of a welded elbow appear to have relatively low strain other than at the shoulders 261, 263. Moreover, the linkage 268 and central peak regions of the elbows 260, 268 appear to experience relatively low strain. Different than the cross-over features associated with Model #2, however, this distribution of the current model is associated with a direct peak-peak weld joint, vs. an actual bridging cross-over features that extends between peaks of the Model #2 design.

5. Model #5

Figure 17:
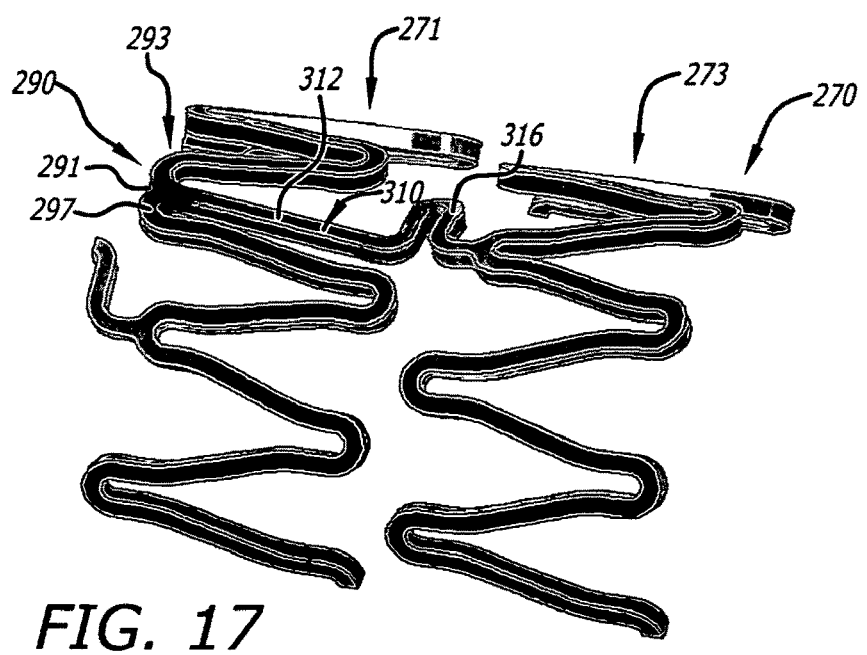
FIG. 17 shows a computer simulation of another representative portion of two adjacent segments of a similar stent model as that shown in FIG. 12 and intended to represent certain aspects of a second commercially available stent, although as subjected to a different lateral bending simulation under computer FEA, and shows shading to reflect varied levels of material strain along the modeled structure in the simulation.

FIG. 17 shows a 3-D FEA simulation and reflecting strain distribution during simulated lateral bending deflection for a two adjacent segment portion of Model #1 as follows. Strain distribution across stent 270 appears to be concentrated mostly in two locations related to the connector 310 interconnecting and extending between the adjacent segments 271, 273. Namely, these locations are at the U-shaped portion 316 transversely oriented along the connector 310 between segments 271, 273, and the end section of the straight portion 312 of the connector 310 that interfaces with and terminates into the valley of crown 290 opposite notch 291 between adjacent bulbs 293, 297. While some slight strain distribution is evidently extending slightly beyond these locations, they are observed to represent fairly focal and isolated strain locations in the simulated bending, with only slight strain artifact propagating therefrom through the surrounding material.

IV. Analysis

A. Expansion Simulation

The expansion simulations performed yielded various observations that distinguish the various models simulated.

Model #1 was observed to exhibit similar strain distribution as that exhibited to Model #4, which each feature localized concentration of strain at inner and outer radii of crown peaks. However, Model #1 exhibits this with a reduced width filament at this region versus adjacent struts extending from the respective crown(s). This allows similar expansion characteristic as if the filament was uniform across these features (as for Model #4), but with additional benefits provided by wider struts at the lower strain regions including without limitation enhanced visibility of the wider strut region and increased surface area here for drug delivery for example. Conversely, if the width of the struts of that model #1 were uniform at the crown peaks with same increased width vs. radial thickness as along the struts, the expansion characteristics would likely be altered, such as for example: requiring higher inflation pressure to produce similar strain at the crowns necessary for expansion; potential for higher recoil; and possibly adverse consequences of twisting of the crowns out of plane when straining a planar structure of higher width than thickness in the circumferential plane.

Model #2 was observed to uniquely distribute strain at the crown shoulders in transition areas to the adjacent struts. This was not observed in other crown designs of the other models. While Model #5 provided certain bifurcated expansion characteristics at some crown areas, these were only at locations of crown-valley connectors, where the crown region itself was bifurcated into two adjacent bulbs on either side of the connector. Outside of these specific limited crowns in that model, the other primary crowns demonstrated similar strain distributions at inner/outer radii of the crown peaks. The Model #2 expansion characteristic is thus unique as compared against all other models simulated or otherwise known.

B. Lateral Bending Simulation

Bending simulation yielded different observations regarding strain distribution between the models simulated, as follows.

Model #1 was observed to exhibit localized bending strain at the cross-overs between segments having reduced width. Model #2 was observed to distribute strain principally at transition regions of struts into two opposite shoulders of the crowns, with no or lowest strain at the crossover regions of increased width versus other adjacent filamental features of the overall structure. This difference in bending strain distribution between crossover designs was observed in Model #3 which included each of these two different crossover features in one stent otherwise carrying segmental features of Model #1. It is believed that the bifurcated bending strain distribution between adjacent shoulder transitions with struts provides a particularly robust approach with certain particular benefits, including for example enhanced fatigue integrity and recoil following radial expansion (or compression).

Model #4 was observed to also bifurcate bending strain to adjacent strut transitions to the crossover feature in that design, but results from direct weld joints that are required between directly confronting crowns of adjacent segments, and in a design with uniform width across the overall filamental structure. The different approach of integral crossovers of increased width extending between facing crown peaks, eg. Model #2, is considered to provide distinct benefits in achieving this resulting strain distribution, including without limitation removing the need for (and various issues associated with) weld joints. Other prior stents that incorporate either connectors or cross-over extensions between adjacent segments generally intend this feature to provide lateral bending flexibility for the stent. However, Model #2 represents a significant departure from this convention, with its respective cross-over region representing a region of locally increased width along the stent filament, and very little if any bending strain localized here (which is transferred in this model to the transition regions adjacent the shoulders).

Model #5 was observed to distribute bending strain along extended flexible connectors, which are provided in that model generally for that purpose.

V. Conclusions

According to the observations made in the expansion and bending simulations performed across the various models, particular benefits are believed to be presented by the unique combinations of features and incumbent performance associated with the designs presented by Model #1, and in particular Model #2.

Example #2

Twenty pigs underwent coronary artery placement of 22 stents of two types as follows: commercially available Driver® stents (n=10); and a physical embodiment similar to that described above with respect to FIGS. 2A-D, referred to here as "Model #2" (n=12) as incorporating similar features as presented for Model #2 in Example #1 simulations presented above. Stents used from each group were provided for intended use in 3.0 mm or 3.5 mm diameter sizes, and were all 18 mm in length. Average vessel diameter at implant was 2.89 mm for the Model #1 group, and 3.04 mm for the Driver® group.

At day 28, animals were re-studied for angiographic endpoints variously represented in Tables 2A-4B. Certain criteria were measured or calculated and included in these Tables as follows. "Balloon-to-Artery" ratio is a measure of balloon oversizing as related to reference vessel diameter at the time of implant. "Acute gain" is the increase in lumen diameter due to stenting, measured immediately post-stent. "Percent stenosis" was calculated via the recognized equation: [1−(in-stent Minimum Lumen Diameter/reference diameter)]×100. "Late Loss" is a calculation of post-stent minimum lumen diameter (measured immediately following implant) minus follow-up minimum lumen diameter (measured at 28 days, here via QCA).

Tables 2A and 2B represent the chronic 28 day restenosis results via QCA for the Driver® group on the whole, and after removing highest and lowest data points, respectively. Tables 3A and 3B represent the chronic 28 day restenosis results via QCA for the Model #2 group on the whole, and after removing highest and lowest data points, also respectively.

The balloon to artery ratios of both groups were similar (1.16±0.06 for the Driver® and 1.14±0.04 for Model #1) which suggests that differences in percent stenosis were not related to differences in injury to the vessels. Negative numbers for follow-up percent stenosis are related to the vessel remaining oversized from initial stent implantation, and not due to aneurysms outside of the stent (e.g. a 14% overstretch may result in some neointimal formation to fill in the overstretch region, with reduction in cross-sectional diameter or area post implantation, yet still produce a negative percent stenosis number so long as the cross-section there remains larger than the reference vessel.

Figure 18:
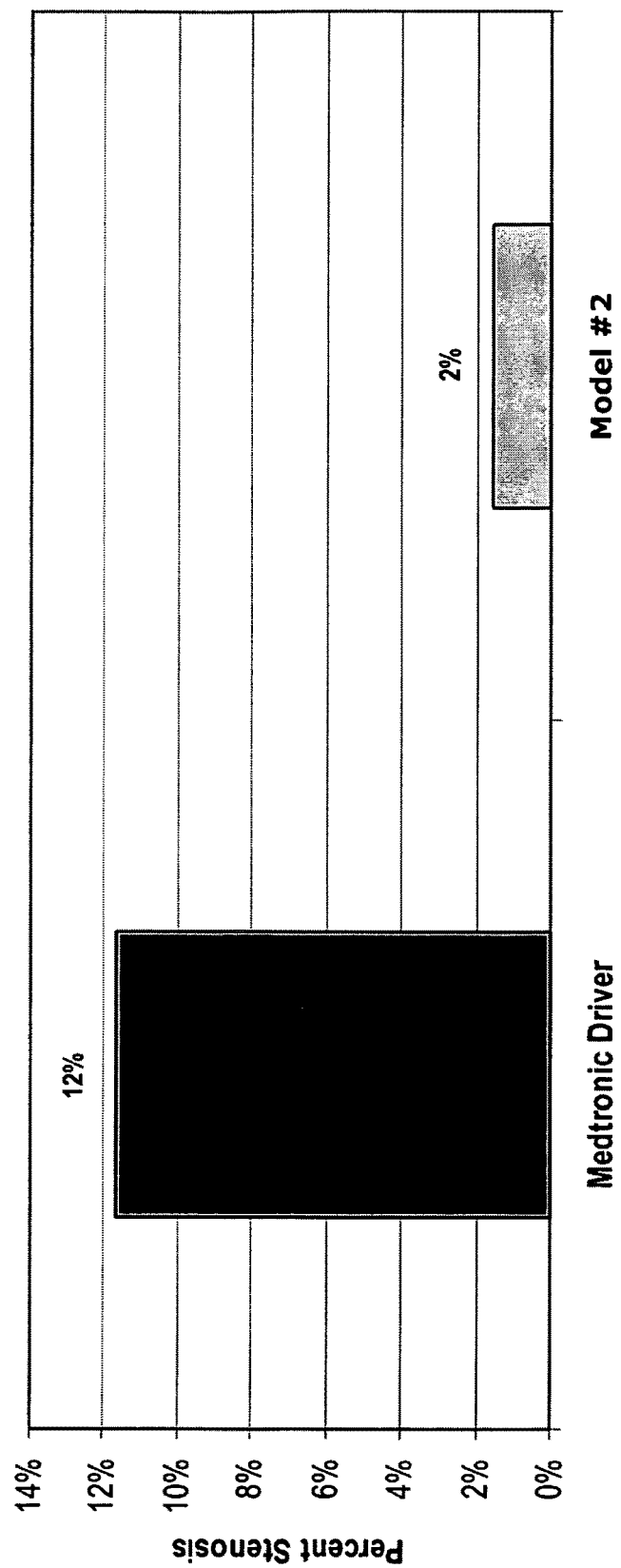
FIG. 18 shows a graph comparing percent restenosis results for two different stent implants according to a pre-clinical 28 day chronic implant study performed.

Table 4A represents the summary Driver® data of Table 2A against the summary Model #2 average data of Table 3A. At day 28, the average percent restenosis results for the Medtronic Driver® group (12%±26%) was 760% greater than that of the Model #2 group (2%±11%). This comparison is further demonstrated in graphical form in FIG. 18. Also compared is the late loss between the test groups. Table 4B shows comparison of average percent stenosis and late loss between the test groups according to the adjusted data of Tables 2B and 3B, respectively. In addition to resulting in substantially lower average percent stenosis than the comparison bare metal stent in this experiment, it is further noted that the average percent stenosis at 28 days for Model #2 results appear similar, or at least close, to percent stenosis results observed at 28 days in similar pre-clinical animal testing conducted for at least one leading drug eluting stent product.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention, to the extent presented by claims appended hereto, is accordingly to be limited by nothing other than such appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. § 112, sixth paragraph, unless the element is expressly recited using the phrase "means for."

TABLE 1

Number of Crossovers and Crossover Positions of Certain Present Embodiments

| Crossover Position | FIG. 1A # of Crossovers 10 Crowns 18 Sections | FIG. 2A # of Crossovers 10 Crowns 18 Sections | FIG. 3A # of Crossovers 9 Crowns 15 Sections | FIG. 4 # of Crossovers 8 Crown 18 Sections | FIG. 5 # of Crossovers 7 Crown 15 Sections | FIG. 6A # of Crossovers 6 Crown 15 Sections | FIG. 7A # of Crossovers 6 Crown 15 Sections |
|---|---|---|---|---|---|---|---|
| 1 | 4 | 4 | 3 | 3 | 2 | 3 | 2 |
|   | (2, 8, 12, 18) | (2, 8, 12, 18) | (2, 8, 14) | (2, 8, 14) | (4, 10) | (2, 6, 10) | (2, 8) |
| 2 | 2 | 2 | 2 | 2 | 2 | 2 | 2 |
|   | (5, 15) | (5, 15) | (5, 13) | (5, 13) | (7, 13) | (5, 11) | (5, 11) |
| 3 | 2 | 2 | 2 | 2 | 2 | 2 | 2 |
|   | (10, 20) | (10, 20) | (10, 18) | (8, 16) | (2, 10) | (2, 8) | (2, 8) |
| 4 | 2 | 2 | 2 | 2 | 2 | 2 | 2 |
|   | (5, 15) | (5, 15) | (5, 15) | (3, 11) | (5, 13) | (5, 11) | (5, 11) |
| 5 | 2 | 2 | 2 | 2 | 2 | 2 | 2 |
|   | (10, 20) | (10, 20) | (2, 10) | (6, 14) | (2, 8) | (2, 8) | (2, 8) |
| 6 | 2 | 2 | 2 | 2 | 2 | 2 | 2 |
|   | (5, 15) | (5, 15) | (7, 15) | (1, 9) | (5, 11) | (5, 11) | (5, 11) |
| 7 | 2 | 2 | 2 | 2 | 2 | 2 | 2 |
|   | (10, 20) | (10, 20) | (2, 12) | (4, 12) | (8, 14) | (2, 8) | (2, 8) |
| 8 | 2 | 2 | 2 | 2 | 2 | 2 | 2 |
|   | (5, 15) | (5, 15) | (7, 17) | (7, 15) | (3, 11) | (5, 11) | (5, 11) |
| 9 | 2 | 2 | 2 | 2 | 2 | 2 | 2 |
|   | (10, 20) | (10, 20) | (4, 12) | (2, 10) | (6, 14) | (2, 8) | (2, 8) |
| 10 | 2 | 2 | 2 | 2 | 2 | 2 | 2 |
|   | (5, 15) | (5, 15) | (9, 17) | (8, 16) | (3, 9) | (5, 11) | (5, 11) |
| 11 | 2 | 2 | 2 | 2 | 2 | 2 | 2 |
|   | (10, 20) | (10, 20) | (4, 14) | (3, 11) | (6, 12) | (2, 8) | (2, 8) |
| 12 | 2 | 2 | 2 | 2 | 2 | 2 | 2 |
|   | (5, 15) | (5, 15) | (1, 9) | (6, 14) | (1, 9) | (5, 11) | (5, 11) |
| 13 | 2 | 2 | 2 | 2 | 2 | 2 | 2 |
|   | (10, 20) | (10, 20) | (6, 14) | (1, 9) | (4, 12) | (2, 8) | (2, 8) |
| 14 | 2 | 2 | 3 | 2 | 2 | 3 | 2 |
|   | (5, 15) | (5, 15) | (5, 11, 17) | (4, 12) | (1, 7) | (1, 5, 9) | (5, 11) |
| 15 | 2 | 2 |   | 2 |   |   |   |
|   | (10, 20) | (10, 20) |   | (7, 15) |   |   |   |
| 16 | 2 | 2 |   | 2 |   |   |   |
|   | (5, 15) | (5, 15) |   | (4, 8) |   |   |   |
| 17 | 4 | 4 |   | 3 |   |   |   |
|   | (2, 8, 12, 18) | (2, 8, 12, 18) |   | (4, 10, 14) |   |   |   |

TABLE 2A

Angiographic results of Driver ® Stents Implanted under Example #2

| Animal Number | Vessel | Description | B/A Ratio | Acute gain (mm) | F/U % stenosis | Late loss (mm) |
|---|---|---|---|---|---|---|
| 3810 | LCX | Driver | 1.14 | 0.40 | 0.0% | 0.10 |
| 3812 | RCA | Driver | 1.22 | 0.60 | 1.9% | 0.70 |
| 3813 | LAD | Driver | 1.23 | 0.70 | −10.3% | 0.50 |
| 3817 | RCA | Driver | 1.07 | 0.20 | 9.7% | 0.40 |
| 3821 | LCX | Driver | 1.20 | 0.50 | 13.8% | 1.00 |
| 3830 | LAD | Driver | 1.21 | 0.50 | 65.5% | 2.40 |
| 3831 | LAD | Driver | 1.09 | 0.30 | 45.7% | 1.90 |
| 3834 | LCX | Driver | 1.19 | 0.60 | −25.9% | 0.30 |
| 3836 | RCA | Driver | 1.09 | 0.30 | 7.1% | 1.20 |
| 3837 | LAD | Driver | 1.15 | 0.40 | 9.1% | 1.30 |
| | | Mean | 1.16 | 0.45 | 11.7% | 0.98 |
| | | SD | 0.06 | 0.16 | 26.3% | 0.74 |

TABLE 2B

Driver ® results of Table 2A following removal of highest and lowest data points

| Animal Number | Vessel | Description | B/A Ratio | Acute gain (mm) | F/U % stenosis | Late loss (mm) |
|---|---|---|---|---|---|---|
| 3810 | LCX | Driver | 1.14 | 0.40 | 0% | 0.10 |
| 3812 | RCA | Driver | 1.22 | 0.60 | 2% | 0.70 |
| 3813 | LAD | Driver | 1.23 | 0.70 | −10% | 0.50 |
| 3817 | RCA | Driver | 1.07 | 0.20 | 10% | 0.40 |
| 3821 | LCX | Driver | 1.20 | 0.50 | 14% | 1.00 |
| 3831 | LAD | Driver | 1.09 | 0.30 | 46% | 1.90 |
| 3836 | RCA | Driver | 1.09 | 0.30 | 7% | 1.20 |
| 3837 | LAD | Driver | 1.15 | 0.40 | 9% | 1.30 |
| | | Mean | 1.15 | 0.43 | 10% | 0.89 |
| | | SD | 0.07 | 0.17 | 16% | 0.58 |

TABLE 3A

Angiographic results of "Model #2" Stents Implanted under Example #2

| Animal Number | Vessel | Description | B/A Ratio | Acute gain (mm) | F/U % stenosis | Late loss (mm) |
|---|---|---|---|---|---|---|
| 3807 | RCA | Model #2 | 1.11 | 0.30 | 0.0% | 0.30 |
| 3812 | LAD | Model #2 | 1.13 | 0.40 | −3.7% | 0.60 |
| 3816 | RCA | Model #2 | 1.13 | 0.10 | 7.4% | 0.60 |
| 3819 | LAD | Model #2 | 1.15 | 0.40 | 0.0% | −0.10 |
| 3820 | LAD | Model #2 | 1.21 | 0.50 | −3.4% | 0.40 |
| 3827 | RCA | Model #2 | 1.16 | 0.50 | −2.9% | 0.00 |
| 3832 | RCA | Model #2 | 1.15 | 0.40 | 10.6% | 1.00 |
| 3835 | RCA | Model #2 | 1.09 | 0.30 | 1.8% | 0.90 |
| 3838 | LCX | Model #2 | 1.14 | 0.40 | −6.7% | 0.10 |
| 3840 | LCX | Model #2 | 1.16 | 0.40 | −10.0% | 0.20 |
| 3825 | LCX | Model #2 | 1.15 | 0.40 | 30.9% | 1.10 |
| 3813 | LCX | Model #2 | 1.07 | 0.20 | −5.7% | 0.20 |
| | | Mean | 1.14 | 0.36 | 1.5% | 0.44 |
| | | SD | 0.04 | 0.12 | 10.9% | 0.40 |

TABLE 3B

Model #2 results of Table 3A after removing highest and lowest data points

| Animal Number | Vessel | Description | B/A Ratio | Acute gain (mm) | F/U % stenosis | Late loss (mm) |
|---|---|---|---|---|---|---|
| 3807 | RCA | Model #2 | 1.11 | 0.30 | 0.0% | 0.30 |
| 3812 | LAD | Model #2 | 1.13 | 0.40 | −3.7% | 0.60 |
| 3816 | RCA | Model #2 | 1.13 | 0.10 | 7.4% | 0.60 |
| 3819 | LAD | Model #2 | 1.15 | 0.40 | 0.0% | −0.10 |
| 3820 | LAD | Model #2 | 1.21 | 0.50 | −3.4% | 0.40 |
| 3827 | RCA | Model #2 | 1.16 | 0.50 | −2.9% | 0.00 |
| 3832 | RCA | Model #2 | 1.15 | 0.40 | 10.6% | 1.00 |
| 3835 | RCA | Model #2 | 1.09 | 0.30 | 1.8% | 0.90 |
| 3838 | LCX | Model #2 | 1.14 | 0.40 | −6.7% | 0.10 |
| 3813 | LCX | Model #2 | 1.07 | 0.20 | −5.7% | 0.20 |
| | | Mean | 1.13 | 0.35 | −0.3% | 0.40 |
| | | SD | 0.04 | 0.13 | 5.6% | 0.37 |

TABLE 4A

Comparison of Driver ® results Table 2A vs. Model #2 results Table 3A

| | Model #2 | Driver ® | % Difference |
|---|---|---|---|
| F/U % Stenosis | 1.5% | 11.7% | 761% |
| Late Loss (mm) | 0.44 | 0.98 | 222% |

TABLE 4B

Comparison of Driver ® results Table 2B vs. Model #2 results Table 3B

| | Model #2 | Driver ® | % Reduction (From Driver ® to Model #2) |
|---|---|---|---|
| F/U % Stenosis | 0% | 9.6% | 100% |
| Late Loss (mm) | 0.40 | 0.89 | 55% |

What is claimed is:

1. An implantable medical stent system, comprising:
a radially expandable stent comprising a filamental structure in a pattern surrounding a bore to form a tubular wall along a length relative to a longitudinal axis;
the radially expandable stent including a plurality of adjacent segments of the filamental structure in series along the length, wherein a series of cross-overs connect adjacent segments, wherein a cross-over extends between certain crown peak-to-crown peak interfaces between adjacent segments; wherein each segment of the plurality of adjacent segments is the same;
wherein the filamental structure comprises at least one arcuate crown with a crown peak having a radius of curvature located along a reference axis, and first and second arcuate crown shoulders on first and second sides, respectively, of the reference axis;
wherein the filamental structure also comprises at least one pair of first and second elongated struts extending from the first and second crown shoulders, respectively; each of the first and second elongated struts have a first radiused region on an edge surface at a first end and a second radiused region on an opposite edge surface at the first end, wherein the first radiused region is staggered with respect to the second radiused region at the first end along each of the first and second elongated struts; and wherein the arcuate crown peak comprises at least one of
(a) a peak width that is greater than at least one of first
and second shoulder widths along the first and second
respective arcuate crown shoulders, (b) an inner radius
of curvature about a second center that is offset from a
first center of an outer radius of curvature, and (c) a
radial expansion characteristic with a strain distribution
that is lower than along at least one of the first and
second crown shoulders; and wherein the filamental structure also comprises a coating
on a surface of the filamental structure.

2. The stent system of claim 1, wherein the coating is at least one of a polymer coating, a non-polymer coating, a radiopaque coating, and a metallic coating.

3. The stent system of claim 2, wherein the polymer coating has zwitterionic pendant groups.

4. The stent system of claim 1, wherein the coating is continuous on the surface of the filamental structure.

5. The stent system of claim 1, wherein the coating is discontinuous on the surface of the filamental structure.

6. The stent system of claim 1, wherein the coating is disposed on an inner surface of the filamental structure.

7. The stent system of claim 1, wherein the coating is disposed on an outer surface of the filamental structure.

8. The stent system of claim 1, wherein the coating is one or more layers.

9. The stent system of claim 1, wherein the coating is bioerodable.

10. The stent system of claim 1, wherein the coating further comprises a bioactive agent.

11. The stent system of claim 10, wherein the bioactive agent is at least one of antineoplastic, antiinflammatory, antiplatelet, anticoagulant, antifibrin, antithrombin, antimitotic, antibiotic, antiproliferative and antioxidant substances, as well as calcium channel blockers, colchicine fibroblast growth factor antagonists, histamine antagonists, 3-hydroxy-3-methylglutaryl coenzyme A (HMG-CoA) reductase inhibitors, monoclonal antibodies, phosphodiesterase inhibitors, prostaglandin inhibitors, platelet-derived growth factor antagonists, serotonin inhibitors, steroids, and thioprotease inhibitors.

12. The stent system of claim 10, wherein the bioactive agent is at least one of rapamycin, cladribine, heparin, nitrous oxide, nitric oxide, actinomycin D, alpha-interferon, genetically engineered epithelial cells, fish oil, des-aspartate angiotensin I, angiotensin converting enzyme (ACE) inhibitors, angiotensin receptor blockers (ARBs), statins, hormones, and estradiol.

13. The stent system of claim 10, wherein the bioactive agent elutes from the coating.

14. The stent system of claim 1, wherein the filamental structure maintains coating integrity.

15. An implantable medical stent system, comprising:
a radially expandable stent comprising a filamental structure of a metal or a metal alloy in a pattern surrounding a bore to form a tubular wall along a length relative to a longitudinal axis;
the radially expandable stent including a plurality of adjacent segments of the filamental structure in series along the length, wherein a series of cross-overs connect adjacent segments, wherein a cross-over extends between certain crown peak-to-crown peak interfaces between adjacent segments; wherein each segment of the plurality of adjacent segments is the same;
wherein the filamental structure comprises at least one arcuate crown with a crown peak having a radius of curvature located along a reference axis, and first and second arcuate crown shoulders on first and second sides, respectively, of the reference axis;
wherein the filamental structure also comprises at least one pair of first and second elongated struts extending from the first and second crown shoulders, respectively; each of the first and second elongated struts have a first radiused region on an edge surface at a first end and a second radiused region on an opposite edge surface at the first end, wherein the first radiused region is staggered with respect to the second radiused region at the first end along each of the first and second elongated struts; and
wherein the arcuate crown peak comprises at least one of
(a) a peak width that is greater than at least one of first and second shoulder widths along the first and second respective arcuate crown shoulders, (b) an inner radius of curvature about a second center that is offset from a first center of an outer radius of curvature, and (c) a radial expansion characteristic with a strain distribution that is lower than along at least one of the first and second crown shoulders; and
wherein the filamental structure also comprises a polymer coating on a surface of the filamental structure.

16. The stent system of claim 15, wherein the coating is continuous on the surface of the filamental structure.

17. The stent system of claim 15, wherein the coating is disposed on an inner surface of the filamental structure.

18. The stent system of claim 15, wherein the coating is disposed on an outer surface of the filamental structure.

19. An implantable medical stent system, comprising:
a radially expandable stent comprising a filamental structure of a metal or a metal alloy in a pattern surrounding a bore to form a tubular wall along a length relative to a longitudinal axis;
the radially expandable stent including a plurality of adjacent segments of the filamental structure in series along the length, wherein a series of cross-overs connect adjacent segments, wherein a cross-over extends between certain crown peak-to-crown peak interfaces between adjacent segments; wherein each segment of the plurality of adjacent segments is the same;
wherein the filamental structure comprises at least one arcuate crown with a crown peak having a radius of curvature located along a reference axis, and first and second arcuate crown shoulders on first and second sides, respectively, of the reference axis;
wherein the filamental structure also comprises at least one pair of first and second elongated struts extending from the first and second crown shoulders, respectively; each of the first and second elongated struts have a first radiused region on an edge surface at a first end and a second radiused region on an opposite edge surface at the first end, wherein the first radiused region is staggered with respect to the second radiused region at the first end along each of the first and second elongated struts; and
wherein the arcuate crown peak comprises at least one of
(a) a peak width that is greater than at least one of first and second shoulder widths along the first and second respective arcuate crown shoulders, (b) an inner radius of curvature about a second center that is offset from a first center of an outer radius of curvature, and (c) a radial expansion characteristic with a strain distribution that is lower than along at least one of the first and second crown shoulders; and wherein the filamental structure also comprises a polymer coating comprising a bioactive agent on a surface of the filamental structure.

* * * * *